United States Patent
Zenhausern et al.

(10) Patent No.: US 12,252,683 B2
(45) Date of Patent: Mar. 18, 2025

(54) WORKSTATION FOR AUTOMATED CONTROL OF AN IN VITRO SYSTEM

(71) Applicant: Arizona Board of Regents on Behalf of the University of Arizona, Tucson, AZ (US)

(72) Inventors: Frederic Zenhausern, Chandler, AZ (US); Matthew W. Barrett, Phoenix, AZ (US); Carla Brooks, Phoenix, AZ (US); Peng Chen, Chandler, AZ (US); Brett M. Duane, Phoenix, AZ (US); Marie Oceane Parent, Phoenix, AZ (US); Stanley D. Smith, Phoenix, AZ (US); Baiju Thomas, Phoenix, AZ (US); Jianing Yang, Phoenix, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 908 days.

(21) Appl. No.: 17/040,427

(22) PCT Filed: Mar. 29, 2019

(86) PCT No.: PCT/US2019/025000
§ 371 (c)(1),
(2) Date: Sep. 22, 2020

(87) PCT Pub. No.: WO2019/191685
PCT Pub. Date: Oct. 3, 2019

(65) Prior Publication Data
US 2021/0079337 A1  Mar. 18, 2021

Related U.S. Application Data

(60) Provisional application No. 62/650,817, filed on Mar. 30, 2018.

(51) Int. Cl.
C12M 1/36 (2006.01)
C12M 1/00 (2006.01)
(Continued)

(52) U.S. Cl.
CPC ............ *C12M 41/48* (2013.01); *C12M 23/16* (2013.01); *C12M 23/34* (2013.01); *C12M 23/46* (2013.01);
(Continued)

(58) Field of Classification Search
CPC ...... C12M 41/48; C12M 23/16; C12M 23/34; C12M 23/46; C12M 25/02; C12M 29/00; C12M 29/10
(Continued)

(56) References Cited

U.S. PATENT DOCUMENTS 6,591,858 B2  7/2003  Peterson
8,268,152 B2  9/2012  Stelzle et al.
(Continued)

FOREIGN PATENT DOCUMENTS

DE  19810901 C1  6/1999
WO  WO 2013/139798 A1  9/2013
(Continued)

OTHER PUBLICATIONS

A microfluidics-based in vitro model of the gastrointestinal human-microbe interface, Shah et al., Nature Communications (Year: 2016).*
(Continued)

*Primary Examiner* — Michael L Hobbs
*Assistant Examiner* — Lenora A Abel
(74) *Attorney, Agent, or Firm* — Leydig, Voit & Mayer, Ltd.

(57) ABSTRACT

Provided are automated cell culture systems and related in vitro cell culture methods, including for a co-culture of
(Continued)

different cell populations having different cell culture conditions. For example, the system may comprise a bioreactor having a plurality of cell culture compartments, the bioreactor having a fluid port fluidly connected to the plurality of cell culture compartments. A pump fluidly connected to the fluid port can provide a cell culture medium to the plurality of culture compartments. A sensor is operably connected to at least one of the plurality of cell culture compartments for measuring at least one cell culture parameter. In this manner, a controller electronically connected the pump and sensor, is configured to automatically adjust a pump flow rate and/or a cell culture gas content to provide a desired steady-state cell culture parameter for facilitating cells interactions and collection of products representative of said interactions.

20 Claims, 24 Drawing Sheets

(51) Int. Cl.
  *C12M 1/12* (2006.01)
  *C12M 3/00* (2006.01)
  *C12M 3/06* (2006.01)
(52) U.S. Cl.
  CPC ............ *C12M 25/02* (2013.01); *C12M 29/00* (2013.01); *C12M 29/10* (2013.01)
(58) Field of Classification Search
  USPC .................................................... 435/284.1
  See application file for complete search history.

(56) References Cited

U.S. PATENT DOCUMENTS

| | | | |
|---|---|---|---|
| 8,647,861 B2 | 2/2014 | Ingber et al. | |
| 9,081,003 B2 | 7/2015 | Park et al. | |
| 10,898,896 B2 | 1/2021 | Zenhausern et al. | |
| 11,221,966 B2 | 1/2022 | Zenhausern et al. | |
| 2006/0127237 A1* | 6/2006 | Shaw ....................... | G01N 1/38 417/313 |
| 2007/0020693 A1* | 1/2007 | Shuler .................... | C12M 41/46 435/7.1 |
| 2009/0269841 A1* | 10/2009 | Wojciechowski ..... | C12M 29/18 435/303.1 |
| 2011/0124035 A1* | 5/2011 | Broadley ............... | C12M 23/28 435/29 |
| 2015/0072413 A1* | 3/2015 | Zenhausern ........... | C12M 29/04 156/291 |
| 2015/0301027 A1 | 10/2015 | Charest et al. | |
| 2016/0145554 A1 | 5/2016 | Ingber et al. | |
| 2017/0107476 A1* | 4/2017 | Polley ................ | G01N 30/8637 |
| 2018/0155665 A1 | 6/2018 | Zenhausern et al. | |
| 2019/0345431 A1 | 11/2019 | Barrett et al. | |
| 2021/0030347 A1 | 2/2021 | Zenhausern et al. | |
| 2021/0199651 A1 | 7/2021 | Zenhausern et al. | |
| 2022/0001378 A1 | 1/2022 | Zenhausern et al. | |

FOREIGN PATENT DOCUMENTS

| | | |
|---|---|---|
| WO | WO 2013/144253 A1 | 10/2013 |
| WO | WO 2014/016379 A1 | 1/2014 |
| WO | WO 2016/189142 A1 | 12/2016 |
| WO | WO 2018/090035 A1 | 5/2018 |
| WO | WO 2020/264385 A1 | 12/2020 |
| WO | WO 2020/264388 A1 | 12/2020 |

OTHER PUBLICATIONS

Shah et al., A microfluidics-based in vitro model of the gastrointestinal human-microbe interface (Year: 2016).*

Accuray Research LLP, (Nov. 2016) "Organ-On-Chip Market Analysis & Trends—Organ (Heart-on-chip, Human-on-chip, Intestine-on-chip, Kidney-on-chip, Liver-on- hip, Lung-on-chip), Application—Forecast to 2025," ReportLinker Nov. 2016, ID: 4311497. Accessed from: https://www.reportlinker.com/p04311497/Organ-On-Chip-Market-Analysis-Trends-Organ-Heart-on-chip-Human-on-chip-Intestine-on-chip-Kidney-on-chip-Liver-on-chip-Lung-on-chip-Application-Forecast-to.html.

Adebiyi et al. (2011) "The use of computational fluid dynamic models for the optimization of cell seeding processes," Biomaterials, 32(34): 8753-8770.

Bilgen et al. (2012) "Modeling of bioreactor hydrodynamic environment and its effects on tissue growth," In: Liebschner M. (eds) Computer-Aided Tissue Engineering. Methods in Molecular Biology, vol. 868, pp. 237-255.

Busek et al. (Feb. 2017) "Microfluidic system for in-vitro hypoxia assays," Proc. SPIE 10061, Microfluidics, BioMEMS, and Medical Microsystems XV, 1006110.

Cremer et al. (Jun. 2017) "Effect of water flow and chemical environment on microbiota growth and composition in the human colon," Proc Natl Acad Sci USA; 114(25): 6438-6443.

Dickman (2013) "Futuristic "human-on-chip" models will drive better predictions for efficacy, safety" Boston Biotech Watch, Nov. 19, 2013. https://bostonbiotechwatch.com/2013/11/19/futuristic-human-on-chip-models-will-drive-better-predictions-for-efficacy-safety/.

Eain et al. (Feb. 2017) "Engineering Solutions for Representative Models of the Gastrointestinal Human-Microbe Interface," Engineering, 3, 60-65.

Egger et al. (May 2017) "Development and Characterization of a Parallelizable Perfusion Bioreactor for 3D Cell Culture," Bioengineering, 4(2): 51.

Elbrecht et al. (2016) "Transepithelial/endothelial Electrical Resistance (TEER) theory and applications for microfluidic body-on-a-chip devices," J. Rare Dis. Res. Treat., 1(3), 46-52.

Henry et al. (Jun. 2017) "Organs-on-chips with integrated electrodes for trans-epithelial electrical resistance (TEER) measurements of human epithelial barrier function," Lab Chip, 17(13): 2264-2271.

Hoyos-Ruiz et al. (2017) "Implementation of ergonomic aspects throughout the engineering design process: Human-Artefact-Context analysis," Int. J. Interact. Des. Manuf. IJIDeM, 11(2): 263-277.

International Search Report and Written Opinion dated Jul. 15, 2019 in International application No. PCT/US2019/025000, 18 pp.

Lentle et al. (2008) "Physical characteristics of digesta and their influence on flow and mixing in the mammalian intestine: a review," J. Comp. Physiol. B, 178(6): 673-690.

Lesher-Perez et al. (Sep. 2017) "Dispersible oxygen microsensors map oxygen gradients in three-dimensional cell cultures," Biomater. Sci., 5(10): 2106-2113.

Maguire (2001) "Methods to support human-centred design," Int. J. Hum.-Comput. Stud., 55(4): 587-634.

Maoz et al. (Jun. 2017) "Organs-on-Chips with combined multielectrode array and transepithelial electrical resistance measurement capabilities," Lab Chip, 17(13): 2294-2302.

Maschmeyer et al. (2015) "A four-organ-chip for interconnected long-term co-culture of human intestine, liver, skin and kidney equivalents," Lab Chip, 15, 2688-2699.

McAlpine (2015) "Human-gut-on-a-chip model offers hope for IBD sufferers," The Harvard Gazette, Dec. 15, 2015. https://news.harvard.edu/gazette/story/2015/12/human-gut-on-a-chip-model-offers-hope-for-ibd-sufferers/.

Nava et al. (2013) "A multiphysics 3D model of tissue growth under interstitial perfusion in a tissue-engineering bioreactor," Biomech. Model. Mechanobiol. 12(6): 1169-1179.

Pasirayi et al. (2011) "Microfluidic bioreactors for cell culturing: A review," Micro and Nanosystems, 3(2): 137-160.

Schuerlein et al. (Aug. 2016) "A versatile modular bioreactor platform for Tissue Engineering," Biotechnol. J., 12(2): 1600326.

Shah et al. (2016) "A microfluidics-based in vitro model of the gastrointestinal human-microbe interface," Nat. Commun., 7:11535. DOI: 10.1038/ncomms11535.

(56) References Cited

OTHER PUBLICATIONS

Sokol et al. (Jan. 2018) "The microbiota: an underestimated actor in radiation-induced lesions?" Gut, 67(1): 1-2.

Takahashi (2011) "Flow Behavior of Digesta and the Absorption of Nutrients in the Gastrointestine," J. Nutr. Sci. Vitaminol. (Tokyo), 57(4): 265-273.

Tanaka et al. (2006) "Evaluation of effects of shear stress on hepatocytes by a microchip-based system," Meas. Sci. Technol. 17(12): 3167-3170.

Timmerman (Oct. 20, 2016) "Organ-On-A-Chip Startup, Emulate, Grabs $45M to Shake Up Drug Discovery," ttps://www.forbes.com/sites/luketimmerman/2016/10/20/organ-on-a-chip-startup-emulate-grabs-45m-to-improve-drug-discovery/?sh=34ac6195fcbf.

Willaert et al. (2015) "Microfluidic Bioreactors for Cellular Microarrays," Fermentation Jan. 2015, 38-78; doi: 10.3390/fermentation1010038.

Yu et al. (2007) "A 3D analysis of oxygen transfer in a low-cost micro-bioreactor for animal cell suspension culture," Comput. Methods Programs Biomed., 85(1): 59-68.

* cited by examiner (bottom) Step and recess features in the lid and the base provide uniform contact pressure during clamping (top) Warping of the lid and the base without step and recess features such that contact pressure is not uniform

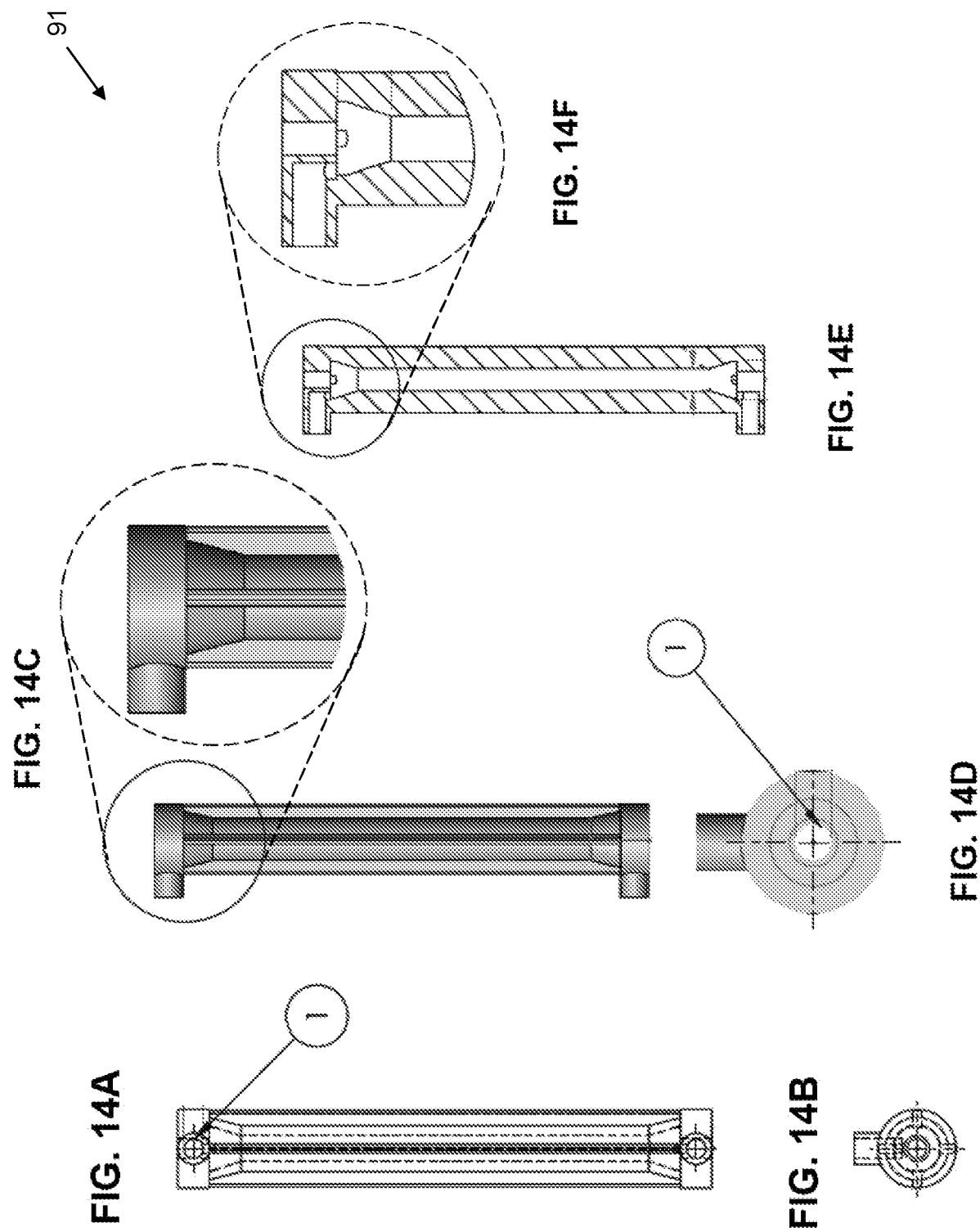

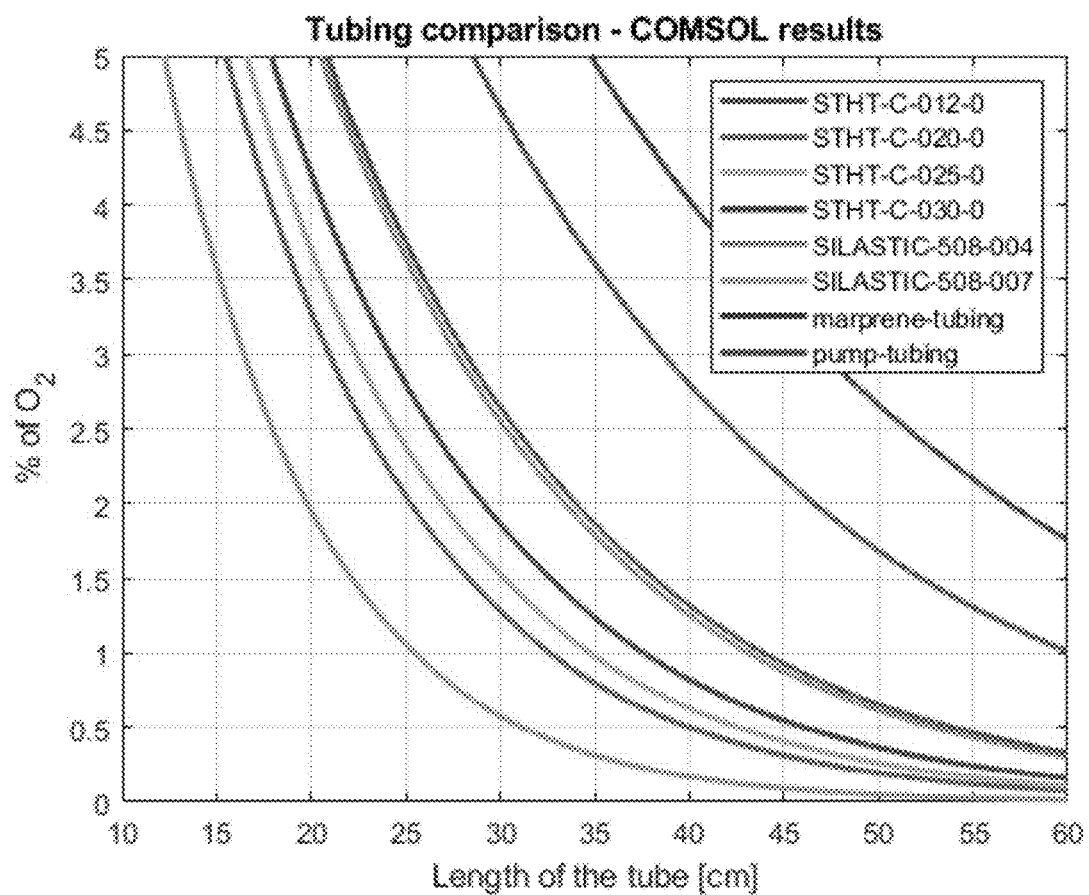
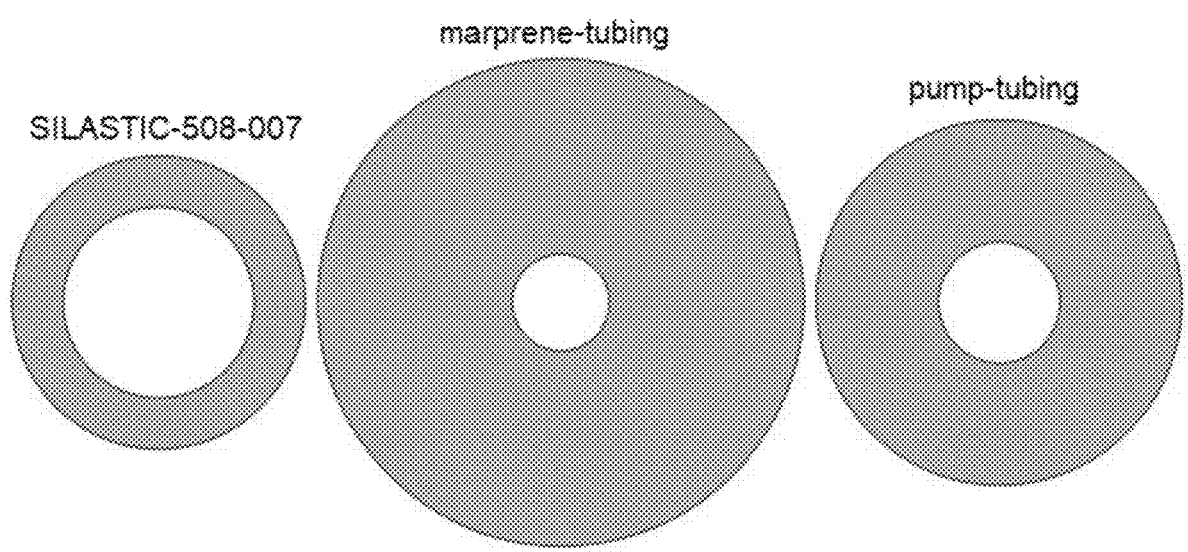
FIG. 25

WORKSTATION FOR AUTOMATED CONTROL OF AN IN VITRO SYSTEM

CROSS-REFERENCE TO RELATED APPLICATIONS

This application is a U.S. National Stage Application filed under 35 U.S.C. § 371 of International Application No. PCT/US2019/025000, filed Mar. 29, 2019, which claims the benefit of U.S. Provisional Application No. 62/650,817, filed on Mar. 30, 2018, which is incorporated by reference herein in its entirety.

STATEMENT REGARDING FEDERALLY SPONSORED RESEARCH OR DEVELOPMENT

Not applicable.

BACKGROUND OF INVENTION

Provided herein are automated modular, microfluidics-based animal-microbial co-culture systems, including for human-microbial co-culture systems. There is a need for development of various components suitable for integration and automated control of culture systems, including bioreactors that culture multiple different cell types (e.g., HumiX bioreactor, WO2013139798, WO2014016379, WO2013144253). In this manner, the various components that are automatically controlled can facilitate remote and reliable operation and collection.

Conventional in-vitro culture systems are limited, particularly for co-culture systems where different cell populations require fundamentally different culture conditions, but are desired to be co-cultured, including for systems where release of bioactive molecules from one cell type affects the other cell type, and vice-versa. The systems and methods presented herein address the problems associated with controlled co-culture in an efficient and stream-lined manner. In particular, the system may be automated, and also has a number of conveniences related to controlling environmental conditions, introducing materials and obtaining materials, including released factors for subsequent molecular analysis, in a manner that ensures the culture remains sterile and ongoing.

The systems and methods have a range of applications, including but not limited to, cell biology research and development, drug discovery, screening and optimization, and in vitro modelling.

SUMMARY OF THE INVENTION

There is a need in the art for improved environmental controls for in vitro modeling systems, including systems where a plurality of different cell types are cultured together. The systems presented herein achieve such co-culture models by having a convenient and reliable bioreactor assembly and disassembly by specially designed screw-in and/or clamping packaging so that different cell types may be confined to different chambers, without sacrificing or adversely impacting the ability to measure culture parameters and/or control inputs to achieve and maintain desired culture parameters. The strategic incorporation of a controller in an integrated configuration and geometry provides the functional benefit of, even for complex multi-culture systems of distinct cell types, a convenient and reliable platform that minimizes risk of contamination and/or cell damage. In this manner, improved cell culture reliability and durability is achieved while saving substantial time and effort.

A controller provides well-controlled manipulation of parameters to ensure ideal or desired cell culture conditions are achieved, including conditions that may vary over time. For example, initial cell seeding into compartments may require different conditions than at a later time after the cells have adhered to a surface and are proliferating, and still different conditions than at even later times as maximum cell density approaches. This controller may be employed in terms of computer-readable instructions (e.g., software) performed by a processor. In this manner, any one or more cell culture parameters are controllable, including in a time-dependent or culture-phase dependent manner, in a remote-controllable and up to a fully automated manner.

The systems provide a high degree of control of environmental conditions such as gas exchange, thereby providing fine-control for culturing of both an animal cell population and a microbial cell population.

The closed-loop nature of the system and methods minimize risk of unwanted contamination while ensuring there are convenient inputs for introducing cell, chemicals, bioactive agents to and from the cell culture compartments.

The automated nature and remote access controls provide the ability to ensure high-quality models and co-cultures are achieved, in a manner that is readily monitored and analyzed. The automated system may control one or more of temperature, moisture, pumping, medium transport, gas exchange, transepithelial impedance monitoring (e.g. TEER), aerobic (e.g. oxygen concentration), anaerobic (e.g. nitrogen levels) and pH sensing. This provides higher-quality monitoring of necessary environmental conditions while improving overall quality and accuracy.

These advantages are achieved by incorporating novel modules in an interconnected manner to obtain an automated workstation system for cell co-cultures, including two or more cell populations. Special user interfaces, including graphical user interfaces (GUI) assists a user in understanding and controlling the culture processes, where the digital information from the system that can be recorded and communicated, while maintaining flexibility often required of very different cell populations.

Provided herein is an automated cell culture system comprising: a bioreactor comprising a plurality of cell culture compartments, the bioreactor having a fluid port fluidly connected to the plurality of cell culture compartments; a pump fluidly connected to the fluid port for providing a cell culture medium to the plurality of culture compartments; a sensor operably connected to at least one of the plurality of cell culture compartments for measuring at least one cell culture parameter; and a controller electronically connected to the pump and sensor, wherein the controller is configured to automatically adjust a pump flow rate and/or a cell culture gas content to provide a desired steady-state cell culture parameter for facilitating monitoring of cell growth and functional maintenance, cell communication and collection of products from cell interactions. Fluid flow and cell culture media composition may be independently controlled and introduced to each chamber. In this manner, fundamentally different cell types (e.g., animal versus bacterial) may be simultaneously cultured within an individual bioreactor.

The bioreactor may be formed from a plurality of stacked layers comprising: a microbial cell culture compartment layer; an animal cell culture compartment layer, wherein the animal cell culture compartment layer is optionally for culturing human epithelial cells; wherein a nanoporous membrane separates the microbial cell culture compartment layer from the animal cell culture compartment layer; and a perfusion microchamber compartment layer, wherein a microporous membrane separates the perfusion microchamber from the animal cell culture component layer; wherein a top substrate layer and a bottom substrate layer are positioned to contain the plurality of stacked layers; wherein the top and/or bottom substrate layers have one or more connectors to facilitate access by one or more sensors to the microbial and/or animal cell culture compartment layers.

The cell culture system may further comprising: a fastener to reliably secure the top and bottom substrate layers and fluidly enclose the bioreactor, wherein the compartment layers are formed of a compressible material, such as a rubber gasket. The fastener may comprise a clamp that compresses the compartment layers upon clamp actuation, including any of the clamp configurations described in WO 2018/090035, hereby incorporated by reference specifically for any of the base, lids, clamps and cell culture support layers described therein that together form a cell culture system having cell culture compartments.

The pump may comprise a controllable pump, wherein an output from the one or more sensors is used to control a fluid flow rate or pressure from the pump. Any of the cell culture systems may comprise a plurality of independently controllable pumps having controlled flow rates of between 1 µL/min to 1 mL/min. In particular, the flow-rate may be selected to achieve a desired shear stress on cells cultured on the wall that faces the flowing culture media, such as in accordance with typically experienced in vivo shear stresses of the biological cells.

An animal cell compartment pump may provide animal cell culture medium to the animal cell compartment and a bacterial cell compartment pump may provide bacterial cell culture medium to the bacterial cell compartment.

The cell culture systems described herein are compatible with a wide range and types of sensors. For example, the sensor may be selected from the group consisting of one or more of: a flow sensor; a temperature sensor; a gas sensor, such as an oxygen sensor (optode); a pH sensor; a chemical sensor; an electrical sensor (electrode); an optical sensor; a relative humidity sensor; and an electromagnetic sensor.

Any of the cell culture systems may comprise a plurality of sensors to measure a plurality of cell culture parameters, wherein the cell culture parameters are selected from the group consisting of one or more of: flow rate; temperature; gas level, such as oxygen, $CO_2$, and/or $N_2$; pH level; chemical level; electric potential (transepithelial electrical resistance (TEER)); optical intensity; relative humidity; pressure; and/or viscosity.

Any of the cell culture systems described herein may have at least one sensor positioned to have direct access to a middle channel of the bioreactor.

Any of the cell culture systems described herein may have a controller configured to provide automated and/or remote control of the cell culture system.

The cell culture system may comprise one or more actuators in electronic communication with the controller to control one or more cell culture parameters, wherein the actuator is selected from the group consisting of a heater, an optical light source, a fluid control element (e.g., valve), a RF communication component (e.g. RF tag, Bluetooth device), and a positioning device (e.g. GPS).

The controller may be part of a computer, and output from the one or more sensors are displayed and/or electronically stored, including on the computer.

The cell culture system may comprise at least four separate bioreactors having independently controllable pumps controlled by the controller.

Any of the cell culture systems may further comprise an incubator having an incubation volume, wherein the bioreactor has a size and geometric shape to fit within the incubation volume. Furthermore, any of the cell culture systems described herein may be characterized as being an "integrated" system, where the various components are provided in a compact footprint with the bioreactors configured as a type of cartridge to facilitate a type of "plug-and-culture" configuration. The ease of connection and removal saves time, increase reliability, and facilitates rapid culture and/or analysis, including at a remote test facility.

Any of the cell culture systems may further comprise electrodes inlaid in a top layer and a bottom layer for continuous monitoring of an electrical resistance in the bioreactor.

Also provided herein are methods of using any of the devices described herein for cell culturing.

For example, provided is a method of co-culturing a plurality of distinct cell types, the method comprising the steps of: providing any of the cell culture systems described herein; establishing a first cell culture in a first cell culture compartment; establishing a second cell culture in a second cell culture compartment, wherein the first cell culture and the second cell culture comprise different cell types; activating the pump to force fluid medium through the fluid compartments at a first fluid flow rate in the first fluid compartment and a second fluid flow rate in the second fluid compartment; monitoring a cell culture parameter in each of the first cell culture compartment and the second cell culture compartment with one or more sensors in each of the cell culture compartments; adjusting the first and/or the second fluid flow rates and/or cell culture gas inflow to maintain the cell culture parameter in each of the first cell culture compartment and the second cell culture compartment; thereby co-culturing the plurality of distinct cell types.

The first cell type may comprise cultured cells from an animal cell-line and the second cell type may comprise cultured bacteria.

The activating, monitoring and adjusting steps may be automatically controlled by a controller receiving output signals from the sensors, wherein the signals output from the sensors are processed and used as part of a feed-back loop in that they at least partially control an input from the controller to one or more actuators to thereby control one or more culture parameters.

The co-culturing may occur for a time period of at least three days without active intervention by a user.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 14. Schematic of a gas exchanger useful for precise gas introduction, including to culture media.

FIG. 25 is a tubing comparison of oxygen concentration as a function of tube length for various tubes, including those graphically represented in the bottom panel (Silastic-508-007; marprene-tubing and pump-tubing, respectively).

DETAILED DESCRIPTION OF THE INVENTION

Figure 1:
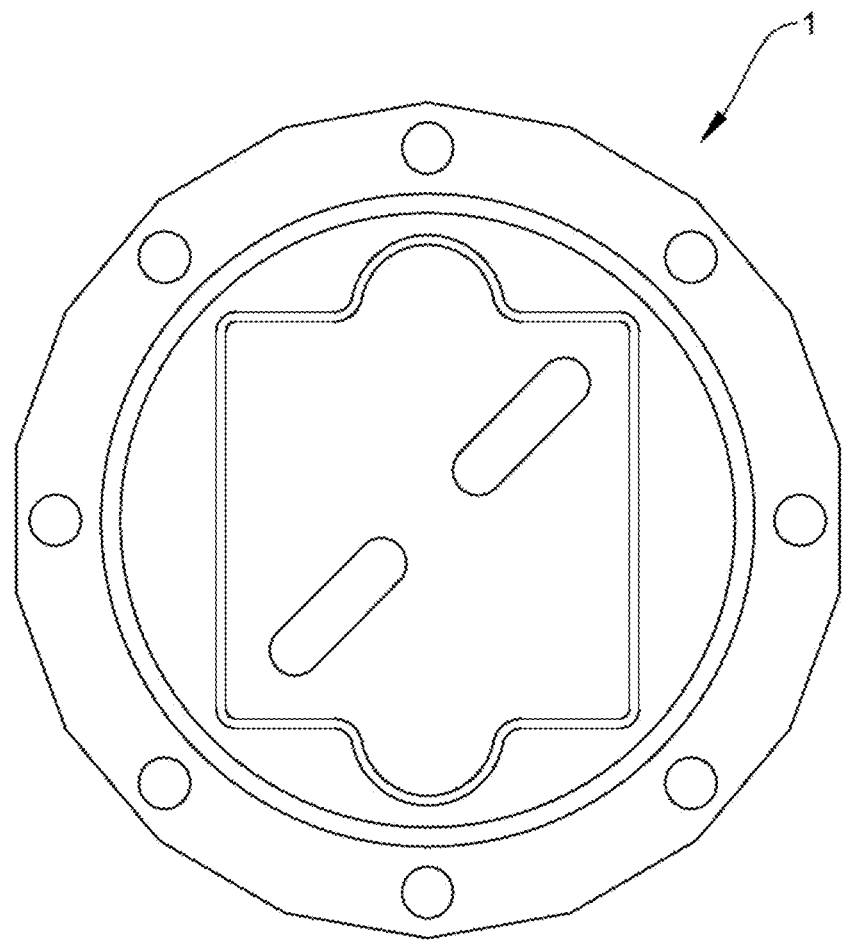
FIG. 1. Micro-gut clamping baseplate.

In general, the terms and phrases used herein have their art-recognized meaning, which can be found by reference to standard texts, journal references and contexts known to those skilled in the art. The following definitions are provided to clarify their specific use in the context of the invention.

"Cell culture parameter" refers to a parameter that affects cell culture growth and well-being. Accordingly, the parameter may related to one or more parameters of the cell culture media, such as oxygen level, carbon dioxide level, pH, temperature, fluid flow rate, and/or the concentration of a substance, such as a nutrient or salt, suspended in the cell culture media. Cell culture parameter may also refer to a parameter of the growing cells, and may include cell number, cell density, electrical parameter such as electrical resistance. Accordingly, depending on the application of interest, such as cell type, one or more cell culture parameters may be monitored, including for use in an automated system wherein action may be taken so as to maintain a desired cell culture parameter for optimum growth, continued growth, and cell maintenance. Furthermore, any of the cell culture parameters may be used to signal when desired cell state, such as cell growth, has been achieved.

"Cell culture compartment" refers to the portion of the bioreactor where cells are placed and cultured. There may be an exchange or transfer of one or more chemicals or biological materials between cell culture compartments, including via diffusion or mass transport through the dividing membranes, but there generally is not an exchange of cells because the cells are confined to their individual compartment.

"Controller" is used broadly herein to refer to the ability of users to automate and/or monitor one or more conditions of the cell culture system, such as $O_2$, pH, temperature, electrical resistance, optical properties or other physicochemical parameters of relevance, etc. The controller may provide one-way or two-way communication. For example, output from the sensors may be transmitted, including wirelessly transmitted, to the controller, which, in-turn, may adjust one or more cell culture parameters, such as a flowrate by control of a pump. This is an example of two-way communication in that the controller is receiving data from the sensors and, in-turn, is sending control signals to active components of the system, such as pumps, thermal actuators, gas input, fluid controllers and valve, including to access an inoculation input. The controller refers to electronic components, including processing chips that provide for communication and control. The controller may, in turn, communicate with an externally located display, such as in a portable device or computer, where a user may be provided with continuous updates of system status or alerts as to one or more user-specified conditions, such as an out-of-range alert or system culture growth completed.

"Active intervention" refers to an individual having to monitor and take active steps so as to maintain desired cell culture conditions. Any of the systems and methods provided herein may be further described as providing "automated" cell culturing in that no person is required to intervene and take active steps in order to maintain appropriate cell culture conditions. This non-active intervention may be described in terms of a time length, including greater than 7-days.

Example 1: Workstation for Automated Control of an In Vitro System

The development of three-dimensional (3D) in vitro models for studying the functional interactions in engineered tissues, microphysiological environments, and organs require accessing the multiple modules and components of a device for preparing the various biological compartments either to set up specific conditions, control operating conditions or more importantly accessing the output materials after a set of reactions or other running experiment using the device. There is also a critical need to integrate and automate the workflow process for operating these in vitro systems, especially when it relates to the synchronization of multiple ancillaries suitable for establishing, maintaining and monitoring the necessary and specific environmental conditions of the systems for optimizing the stability, reproducibility and accuracy of the overall physiological parameters of the system. Provided herein are workstation systems and related methods with novel modules that can be interconnected for controlling the multiple processing steps (e.g. pumping, medium transport, gas exchange, oxygen and pH sensing) to facilitate the biological functions required for in vitro cell biology. The workstation also facilitates the user interface by automating the fluidic systems, monitoring measurements and digital information recording and communication, while addressing flexibility of different processing conditions with application-specific culture environment.

The device assembly may comprise a multiple layered microfluidic reactor, integration of physico-chemical monitoring sensors (e.g. optical oxygen sensor and electrochemical TEER biophysical measurement) and the software control of pumping devices and other fluidic but also thermal actuators and incubation system.

This is also a functional improvement on previous inventions declared under WO2013139798, WO2014016379, WO2013144253, PCT/EP2016/062024 (U.S. Provisional 62/166,940) and PCT/US2017/061602. Although those cases report a microfluidic bioreactor for performing co-culture cell biology, there is a need for the workstation approach described herein, in particular for the integration and automated control of the environmental conditions for co-culture. Typically in vitro micro-physiological systems or organ-on-chips used in tissue engineering and co-culture systems require complex environmental controls including cumbersome equipment for incubation. The systems and methods address the following requirements:

1. Bioreactor assembly by removing of clamping mechanism by a screw-in packaging with precise threading for controlling the pressure evenly on the device assembly allowing readily opening/closing for accessing the biological materials.

2. Software assisted automation of all the fluidic system ancillaries for precise and calibrated processing suitable for remote use.

3. Design of ancillary components to better control the gas exchange for adjusting the various types and ratios of gases.

4. Integration of the environmental media and environmental components in a close loop system for improving control and simplifying incubation instrumentation replacing commercial large and expensive instruments.

5. Automated and remote access for controlling all sensing and other metrological devices for in situ monitoring.

Example 2: ANBM Organ on a Chip (OAC)

The OAC device comprises multiple layers of polycarbonate and medium durometer rubber. The layers are to contain the three channels required to force interaction between the human cells (e.g., Cacao2 or primary cells, ultimately) cells and the biome of the bacteria that exists either in the human digestive track or the oral cavity, upper respiratory tract, skin, blood circulation or other tissue systems.

Three layers are required for the Micro-Biome study. These layers should be considered channels that rest atop each other, separated by micro-membranes, allowing the cells and bacteria to interact indirectly. The current design is optimal for Three (3) flowing channels, with no 'dead' space within, so that all cells receive the same media mixture of $O_2$, $N_2$, and $CO_2$. 'Dead' space would create areas of non-growth or non-communication.

To contain the three channels, solid (e.g, polycarbonate) plastic is machined with various support structures to facilitate access to flow and measurement tools. For example, barbs are machined into the plates on both sides, for connections without leakage. The current micro-gut device is 2.5" square. However, the clamping mechanism that keeps the device secure and free of contamination is 4.75" round.

The baseplate or bottom substrate layer 1 shown in FIG. 1 is fabricated from one solid piece of machine quality polycarbonate plastic. Optical quality is reduced significantly due to machining marks from the CNC process but optically-grade plastics may also be used.

Figure 2:
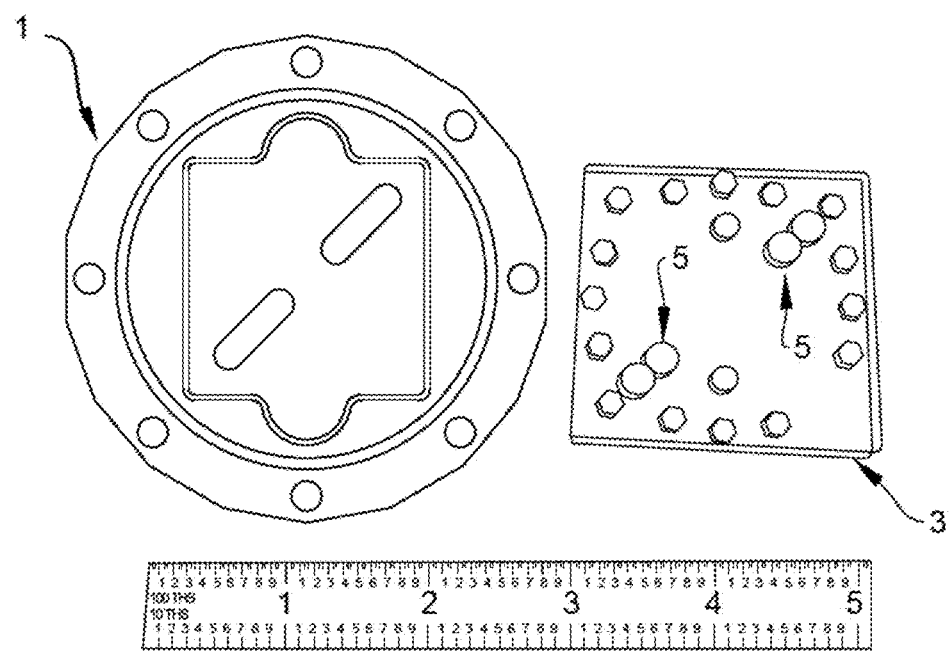
FIG. 2. Baseplate and First Containment plate.

The plate thickness is 3 mm. The first containment plate or top substrate layer 3 shown in FIG. 2 is 5.74 mm thick polycarbonate plate. It has optical clarity typical of un-machined polycarbonate. The reason it is this thickness is because the hose barbs 5 used to connect to the inner channels 7 of the gaskets 9 are machined out of the same plate. This facilitates reuseable plates 3 that require repeated auto-claving. Threaded or glued barbs 5 would not withstand the autoclave process more than once or twice.

Figure 3:
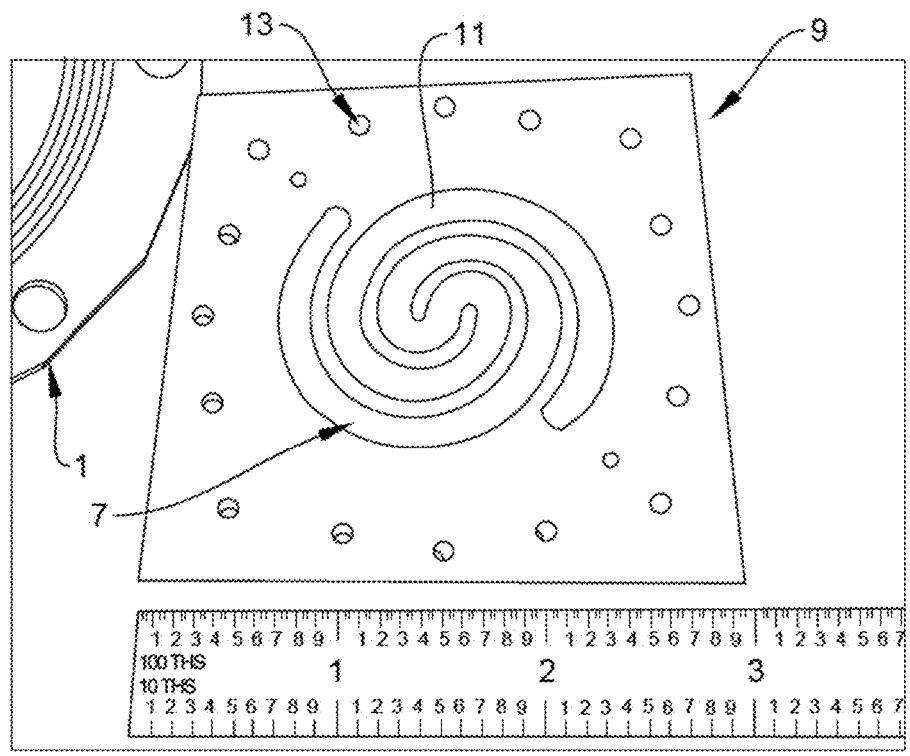
FIG. 3. Gaskets and membranes to form a plurality of cell culture compartments.

FIG. 3 shows rubber gaskets 9 with the polycarbonate membranes 11 attached by adhesive. The membranes 11 are extremely thin, less than 0.01 mm thick and the gaskets 9 are 0.73 mm each, totaling 2.19 mm, that together form distinct cell culture compartments 7, also referred generally as channels. After compression, the total thickness is closer to 2 mm.

Figure 4:
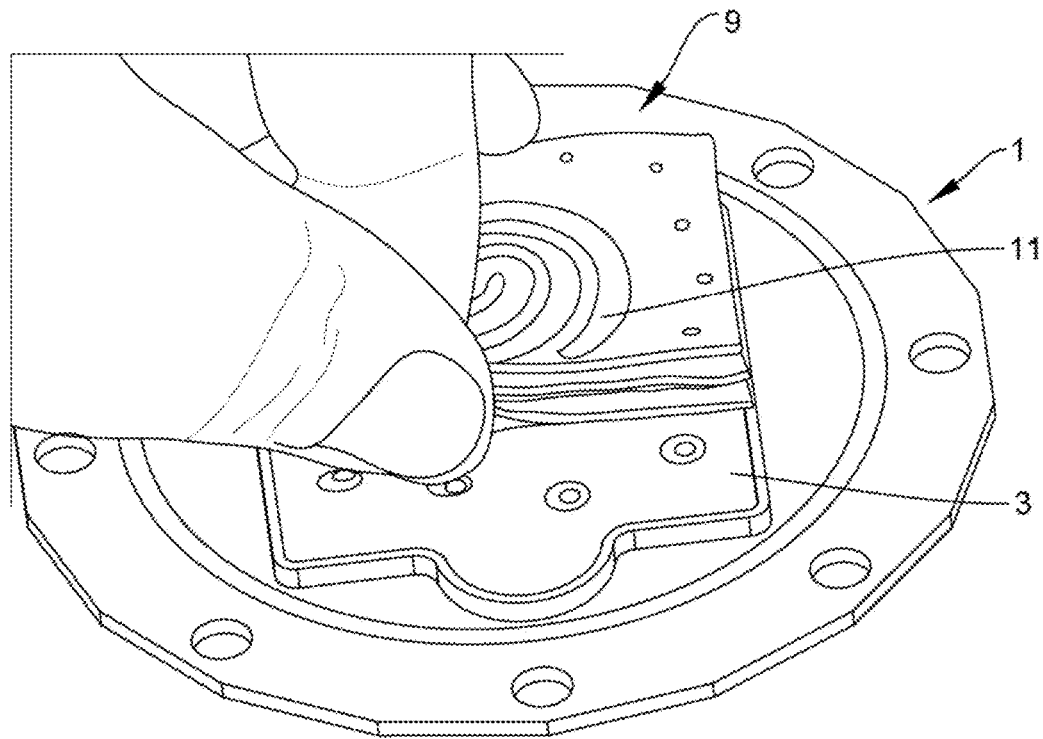
FIG. 4. Baseplate, containment plate, and three gaskets aligned being placed into the containment plate.

The gaskets 9 align using pinholes 13 that surround the edge of the gasket 9. The gaskets 9 drop in on top of the polycarbonate containment plate 3 during assembly, as shown in FIG. 4.

Figure 5:
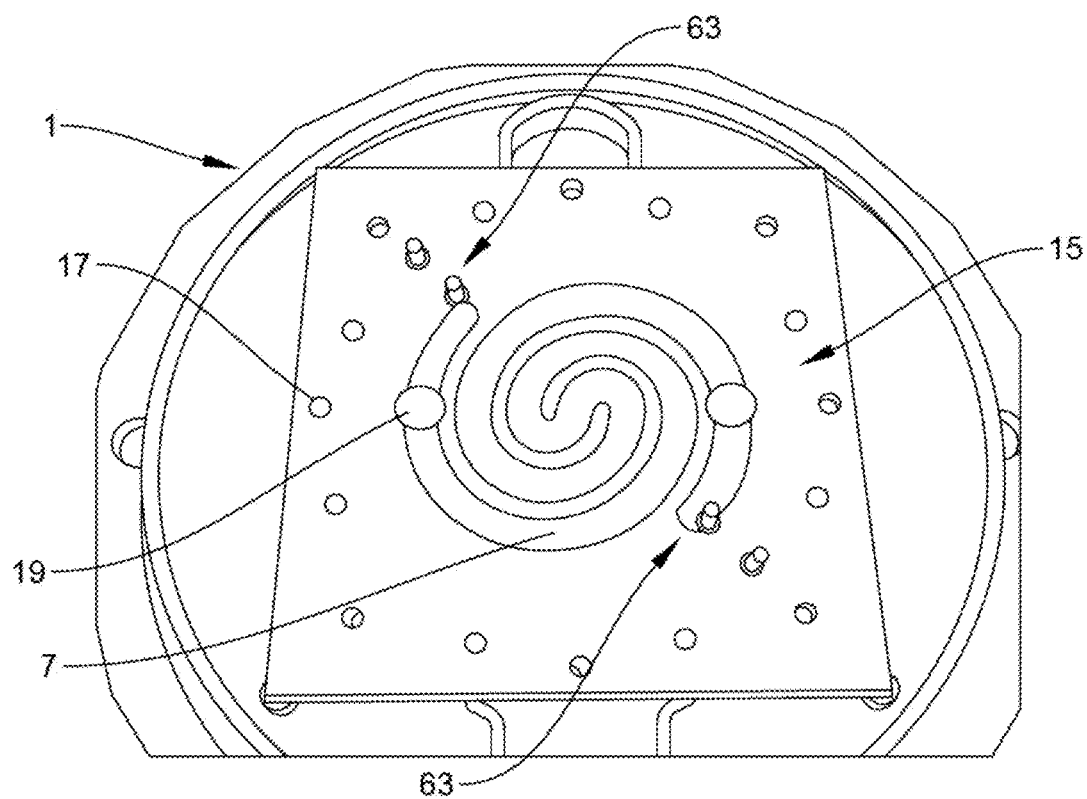
FIG. 5. Top containment plate with fluid ports (Barbs Machined).

FIG. 5 shows the upper containment plate 15 with pin-holes 17 for alignment and machined barbs 5. The small dimples 19 are facing the channels 7 (inside). These are used for spaces to hold optodes 83 for conducting $O_2$ measurements. The ports 63 for fluid flow are visible.

Figure 6:
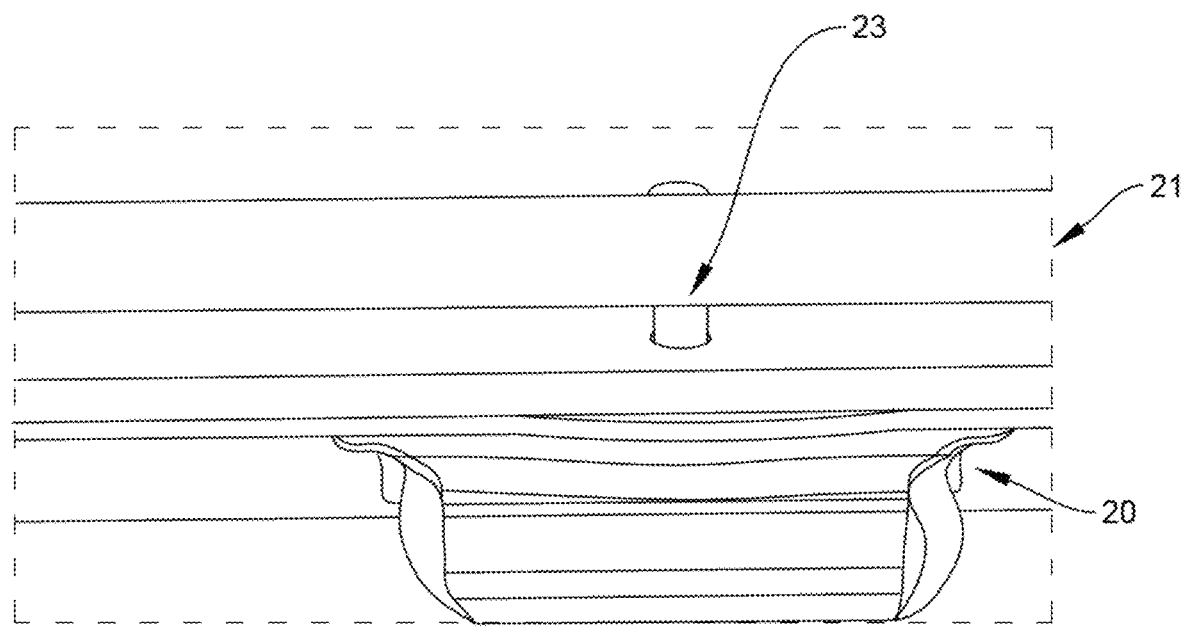
FIG. 6. Pressure plate with alignment pins.

FIG. 6 shows the stack 20 in the plates 1 with the upper pressure plate 21 (with pins 23) pressed on top.

Figure 7:
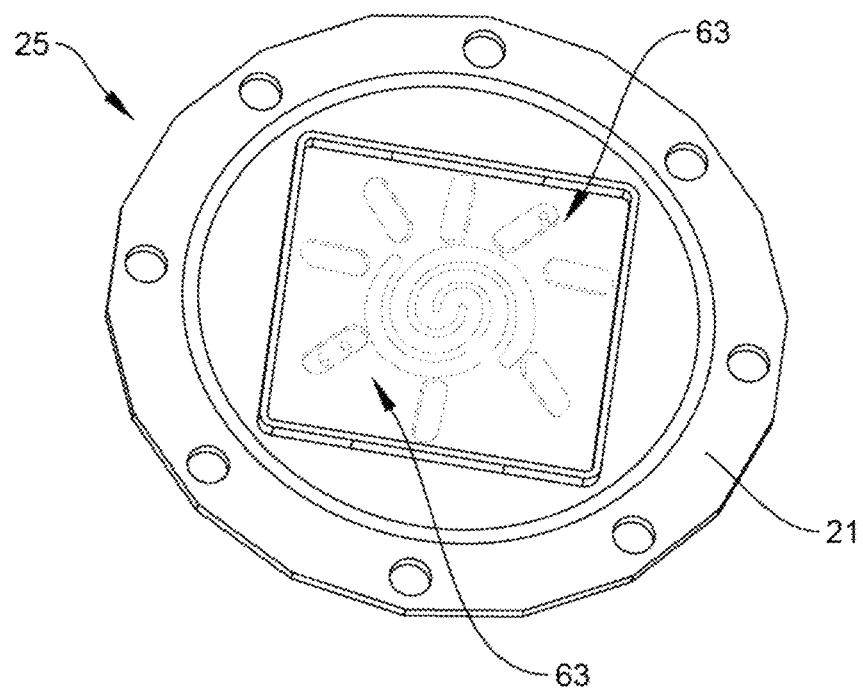
FIG. 7. Sealed Micro-gut (all pieces) with a total thickness of about 20 mm.

FIG. 7 is the full micro-gut device 25, clamped between the plate system, which is threaded and tightened to create a sealed, leak-free environment. The pressure plate 21 thickness+the containment plate 15 thickness is equal to 8.8 mm, all made from the same polycarbonate materials.

Figure 8:
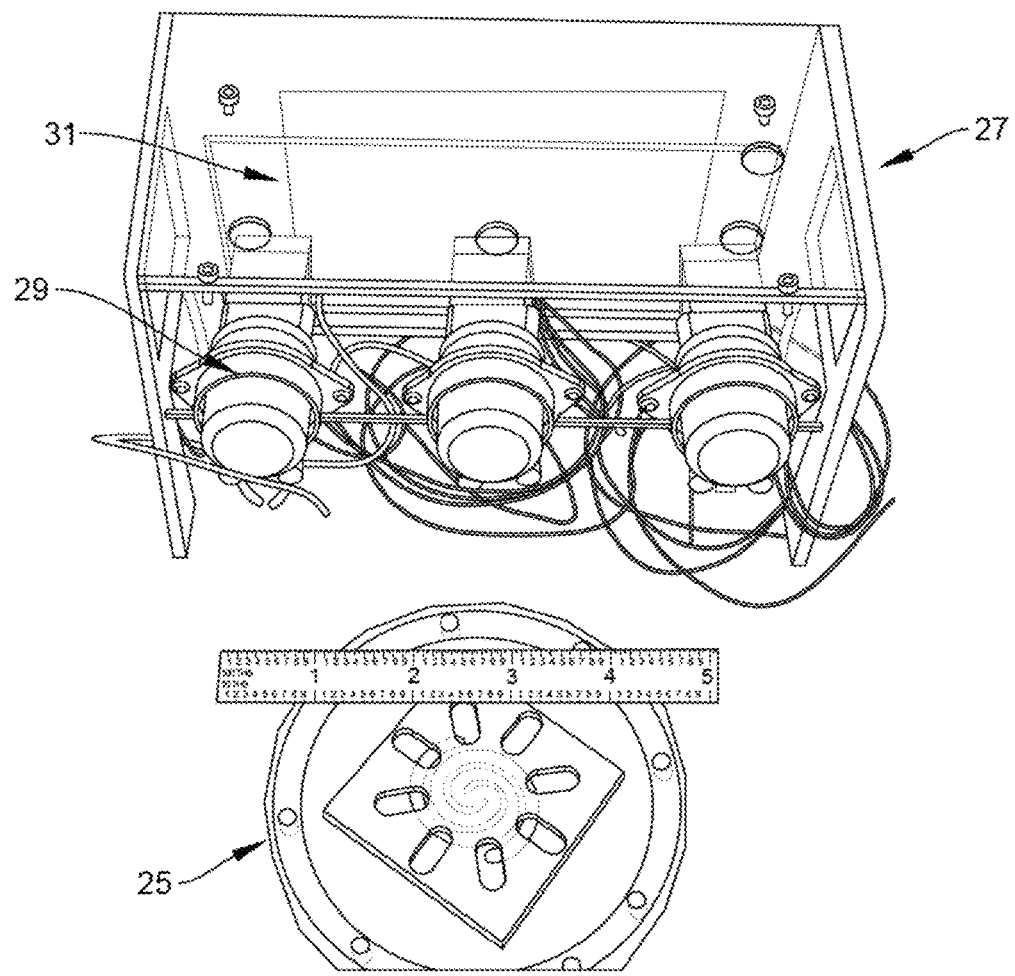
FIG. 8. Micro-gut, clamp and pumping system.

As shown in FIG. 8, the full pumping system 27 comprises three micro stepping pumps 29, circuit-board controller 31 and software. The software can be loaded on any suitable operating system (e.g., Microsoft® Windows) with USB support. The pumps 29 can then be controlled individually by direct input of the require volume-per-minute flow (e.g., μL/min).

Example 3: Technical Specifications

Presented herein is a functional specification for the delivery of a High-Throughput HuMiX system including the automated instrument with controllers for ancillaries (e.g. environmental control for incubation) and the associated bioreactors where the co-culture can occur. Feasibility for remote control of a HumiX system for space flight application under a framework for long term exploration is provided herein.

Figure 9:
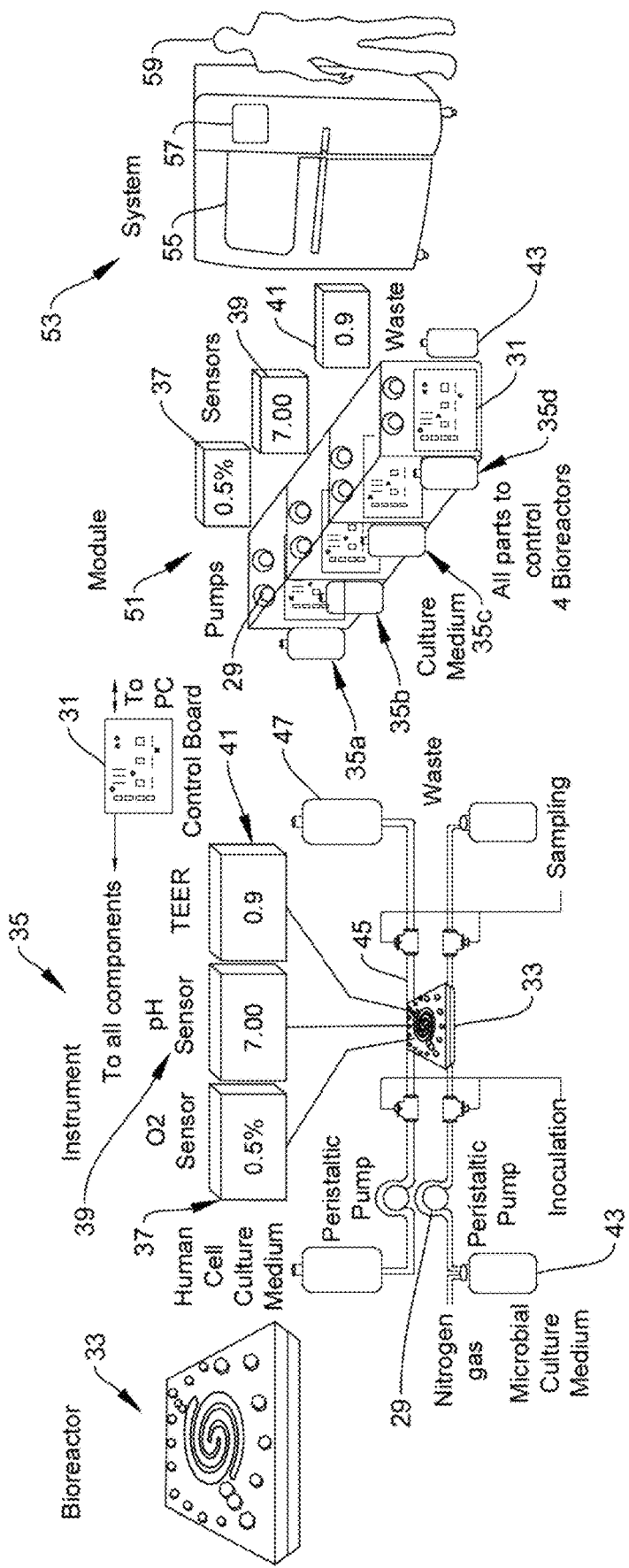
FIG. 9. Schematic illustration of workstation with various system components.

As shown in FIG. 9, the exemplary system is composed of the following components:

Bioreactor 33—The basic cartridge structure comprised of three (or more) layers of chambers and the associated ports 63 and connections to run the bioreactor 33 (also called cartridge, device, reactor). The bioreactor 33 may include, at least in part, the aforementioned features of the micro-gut device 25, as shown and described above with reference to FIGS. 1-7.

Instrument 35—One bioreactor with corresponding pumps 29, pump motor drivers 56, monitoring systems ($O_2$ sensing devices 37, pH 39, TEER 41, etc.) and other required components (e.g., fluids 47, tubing 45, waste 43, etc.) needed to run the bioreactor 33, including control board 31, but not including the controlling personal computer (PC) 57 or incubator 55.

Module 51—A set of 4 Instruments (e.g., 35a, 35b, 35c, 35d, complete with bioreactors 33, control boards 31, fluid 47 source and waste 43 supplies, etc.).

Figure 15:
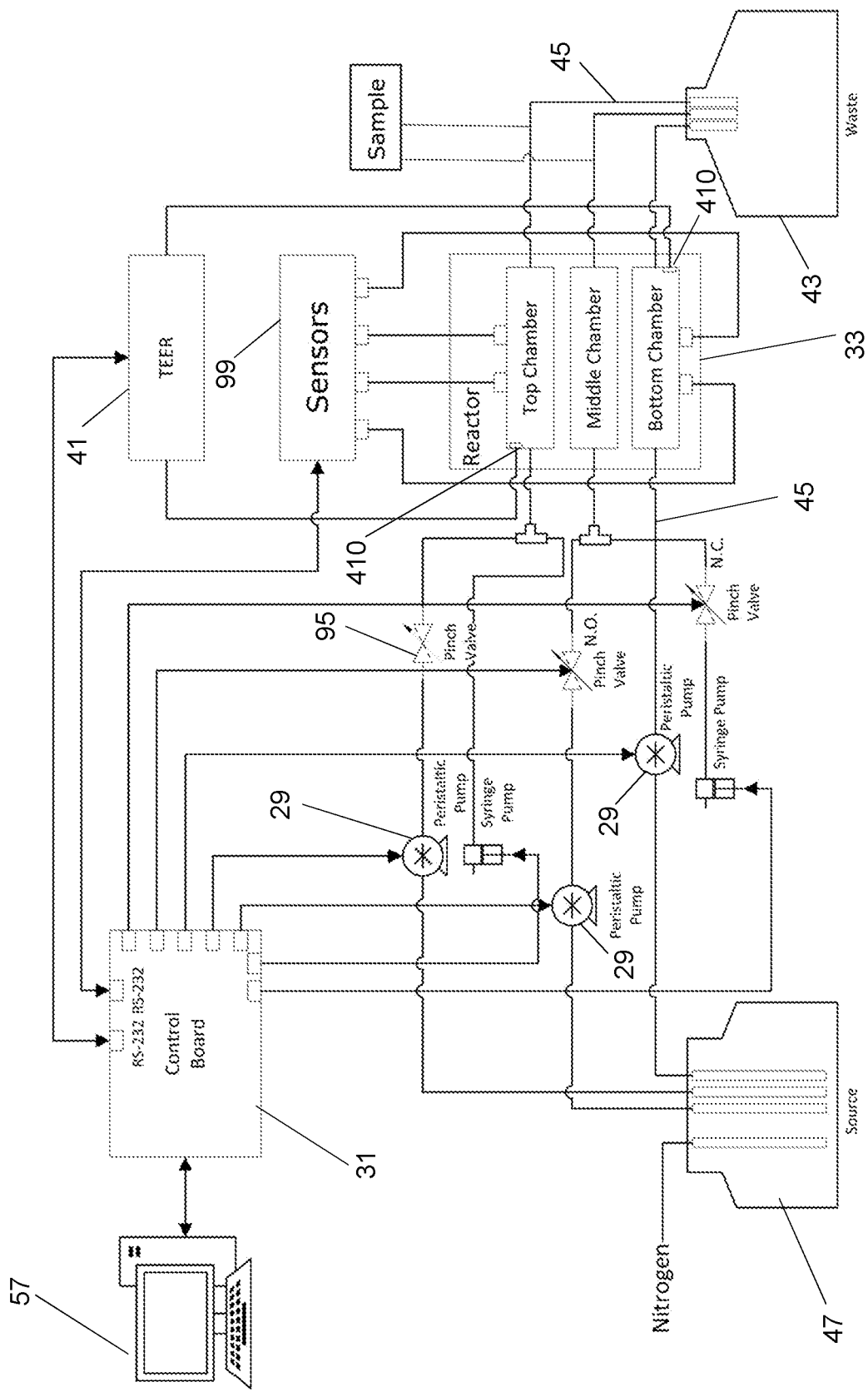
FIG. 15. Schematic block diagram of a cell culture system with automated operations.
Figure 16:
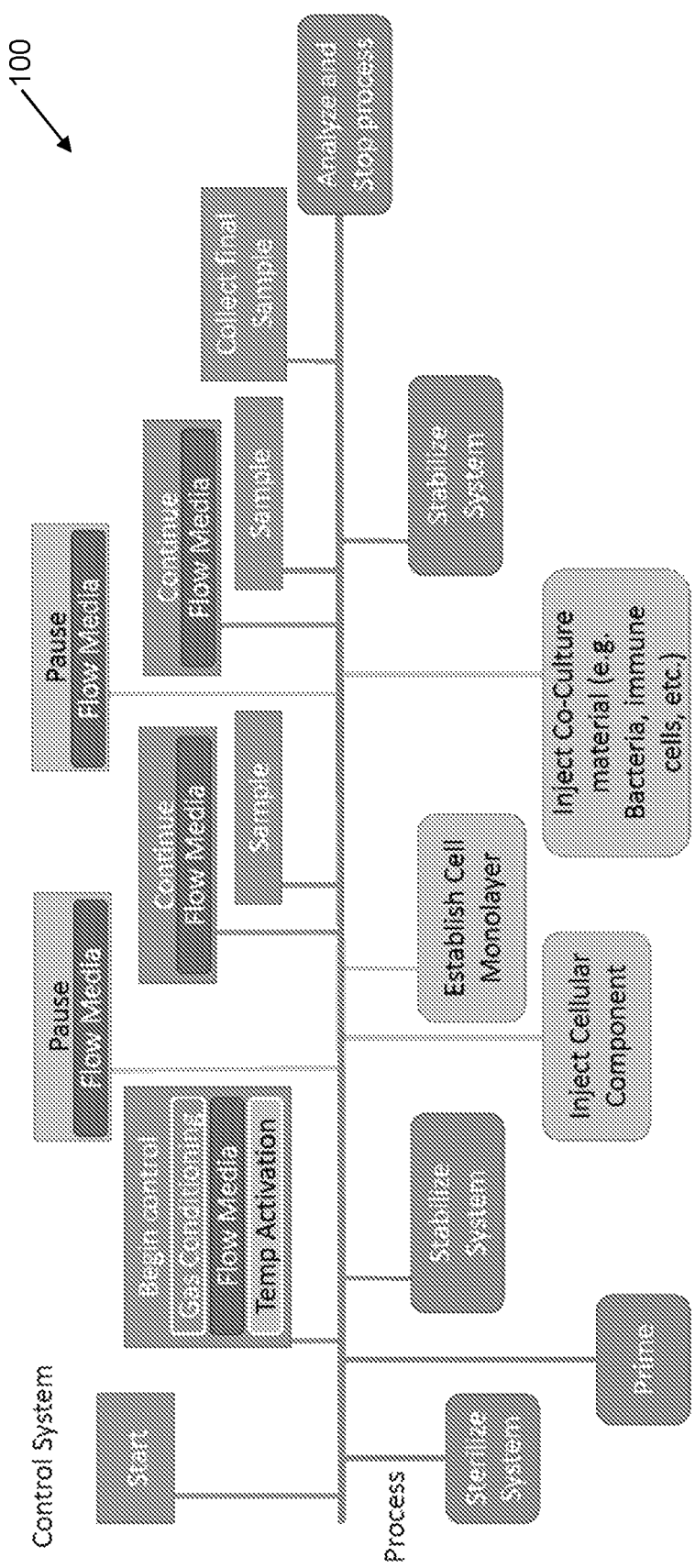
FIG. 16. Process flow summary of automated control of a bioreactor, including a co-culture bioreactor system, including cell introduction, growth, and collection steps.

System 53—A complete system 53 includes an incubator 55, a host PC 57 to run it, and necessary connections, controls, gases, etc. to operate automatically up to 100 instruments, including absent any intervention by a human user 59. The schematic process and instrumentation diagram of FIG. 15 may be utilized, at least in part, in operation of the system 53 shown in, and described with reference to, FIGS. 9, 18 and 19 (integrated system with improved modularity). The process flow 100 summary shown in FIG. 16 of automated control of a bioreactor 33, including a co-culture bioreactor system, including cell introduction, growth, and collection steps may be employed for operation of the system 53 shown in, and described with reference to, FIGS. 9 and 18. Various technical considerations are summarized in the Tables section, Tables 1-10.

Example 4: Gasket and Lid Change

Objective: To find a point on the Humix device (e.g., bioreactor 33) to allow $O_2$ measurements of the middle channel. Currently, the optodes 83 used in the measurement of the $O_2$ concentration of the medium fluid 47 only have access to the outer channels 85 of the 3-channel system 81. In this example, an option is explored for measuring the $O_2$ level of the current middle channel of the 3-channel system 81 with minimal changes to the structure.

Figure 10:
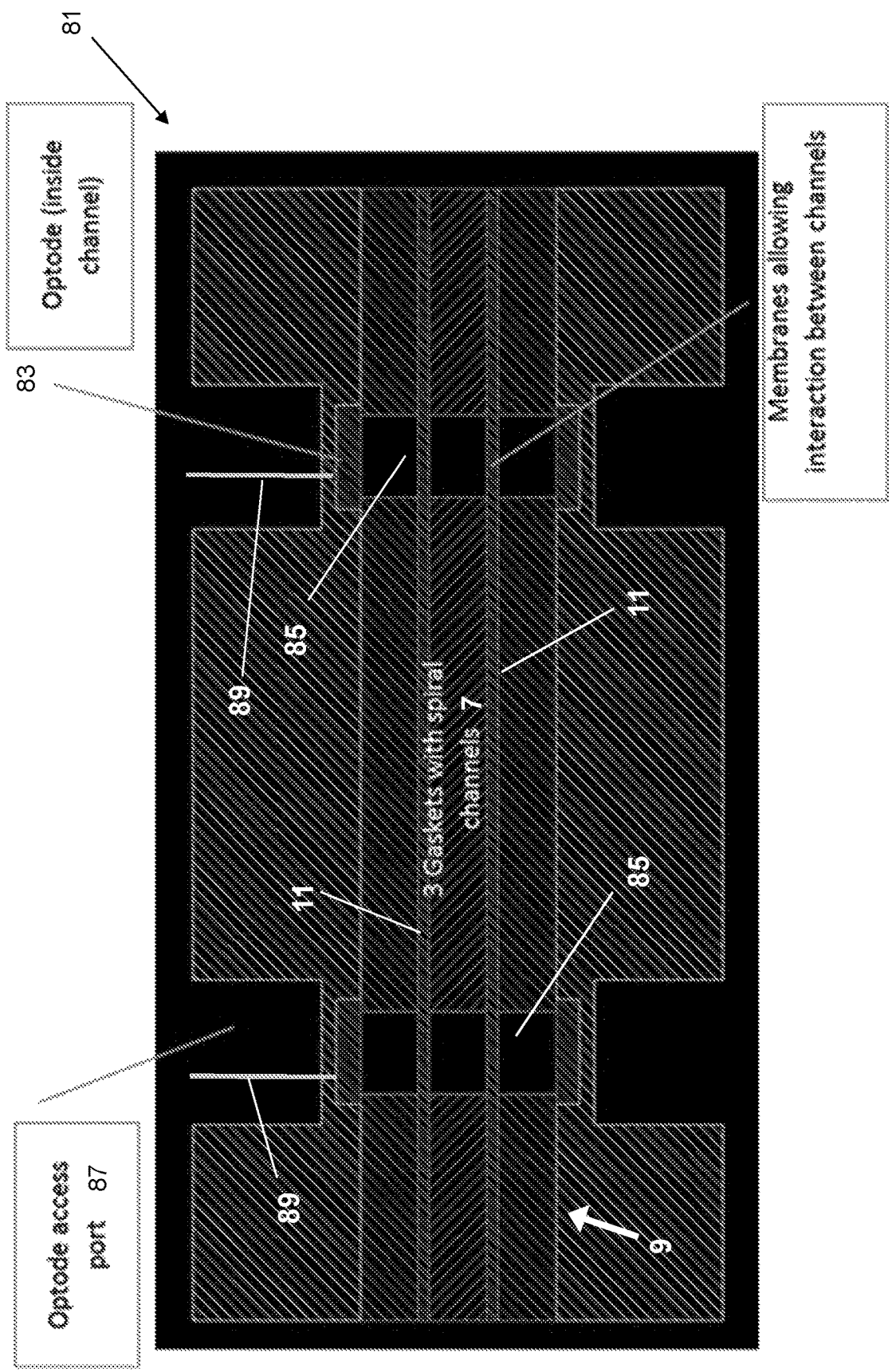
FIG. 10. Cross-section of simple gasket and lid stack-up.

Description: In a previous system (FIG. 10), each gasket 9 has a spiral channel that overlays the channels of the other two layers separated by nano-pore membranes 11. The optodes 83 can only read the outer channels 85 because the optode 83 is mounted to the inside of the press plate 21 and is unable to reach the inner channel 7. This convenience gives access to the optical fiber that reads the optode 83 disc. The inner channel 7 cannot be read because the glass optode 83 discs cannot be mounted inside the inner channel 7.

Figure 11:
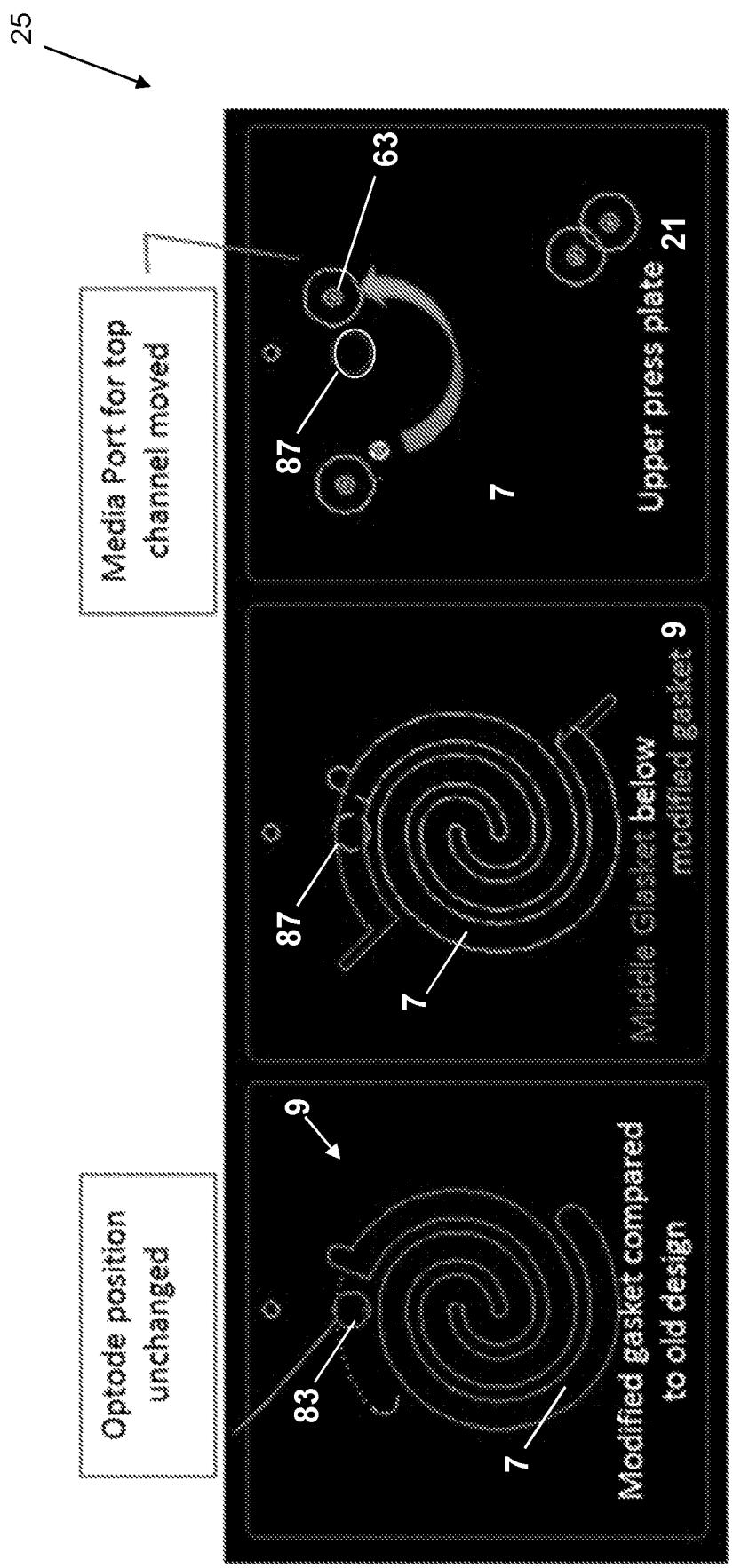
FIG. 11. Gasket and lid modifications to provide physical access to middle culture chamber.

In the example shown in FIG. 11, one of the outer channels 85 is shortened by ~1/10th its normal spiral length near one of the ports 63. In the area that would normally be an optode 83 port 87 for the outer channel 85 now is beyond the reach of the shortened channel. The gasket 9 now has a hole through it just below the optode 83, which allows the optode 83 direct access to the medium fluid 47 of the inner channel 7, previously not possible. The surrounding gasket 9 material prevents the medium fluid 47 of the inner channel 7 from mixing with the medium fluid 47 of the shortened channel.

The fluid port 63 that feeds media fluid 47 is also moved to reach the shortened channel. To keep it relatively easy to access, the port 63 is moved enough to allow the optode 83 fiber-optic cable 89 unhindered access to the optode 83, as well as giving enough room for the user 59 to plug-in the media fluid port 63 tubing 45.

These changes require a redesign of the gaskets 9, the dual-port 63 lid and the clamping mechanism to ensure access to the changed device 25. All changes are made in-house, including gasket 9 changes. Currently, focus is to define the cutting parameters needed for the $CO_2$ laser cutter/scriber so that the gaskets 9 can be crafted with minimal debris and cost.

Example 5: Humix Pump Controller

Figure 12A:
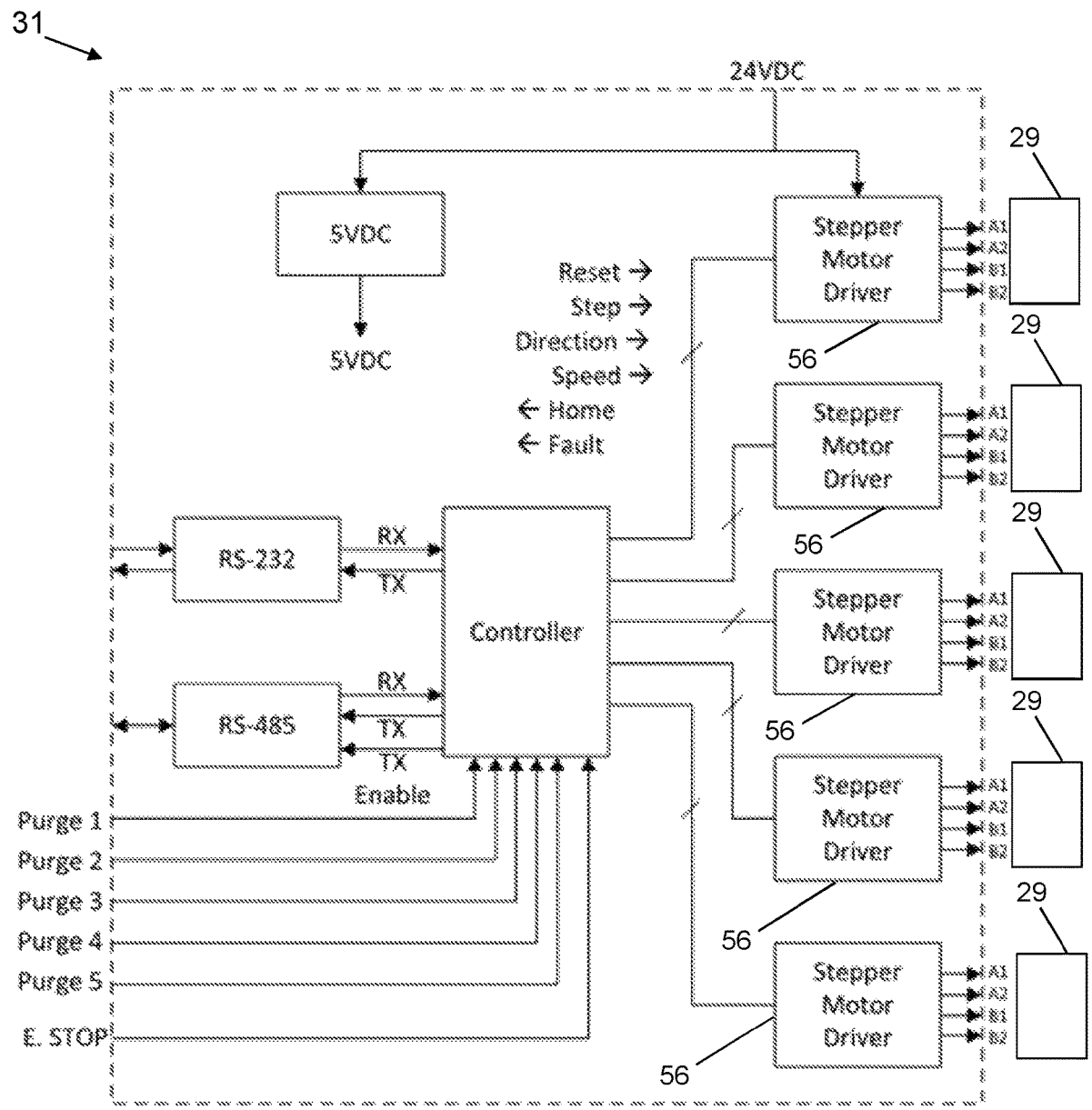
FIGS. 12A-12B. Illustrations of the various components for controlling the fluidic pumping within the HuMiX device.
Figure 12B:
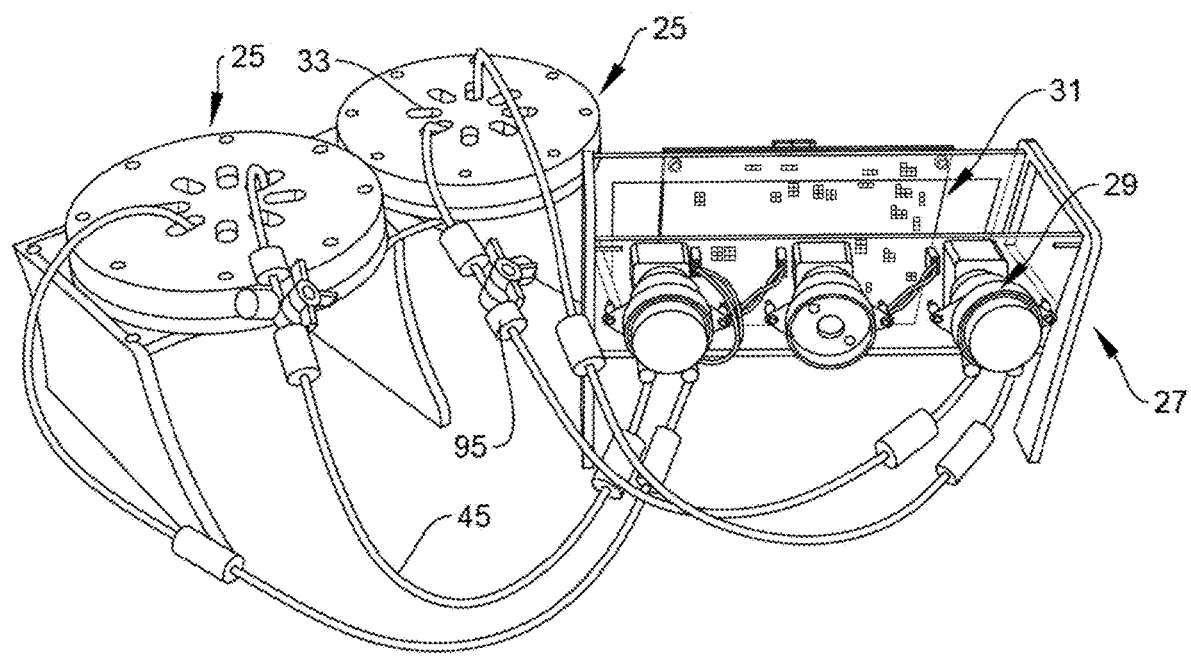

FIGS. 12A and 12B are illustrations of the various components for controlling the fluidic pumping within the HumiX device, including by a microfluidic pump such as a pump 29 driven with a stepper motor that provides highly accurate flow-rate, when controlled by, for example, the motor driver 56 and other analog and/or digital electronic components of control board 31.

Example 6: Step Feature of the Buckle Clamp

Figure 13A:
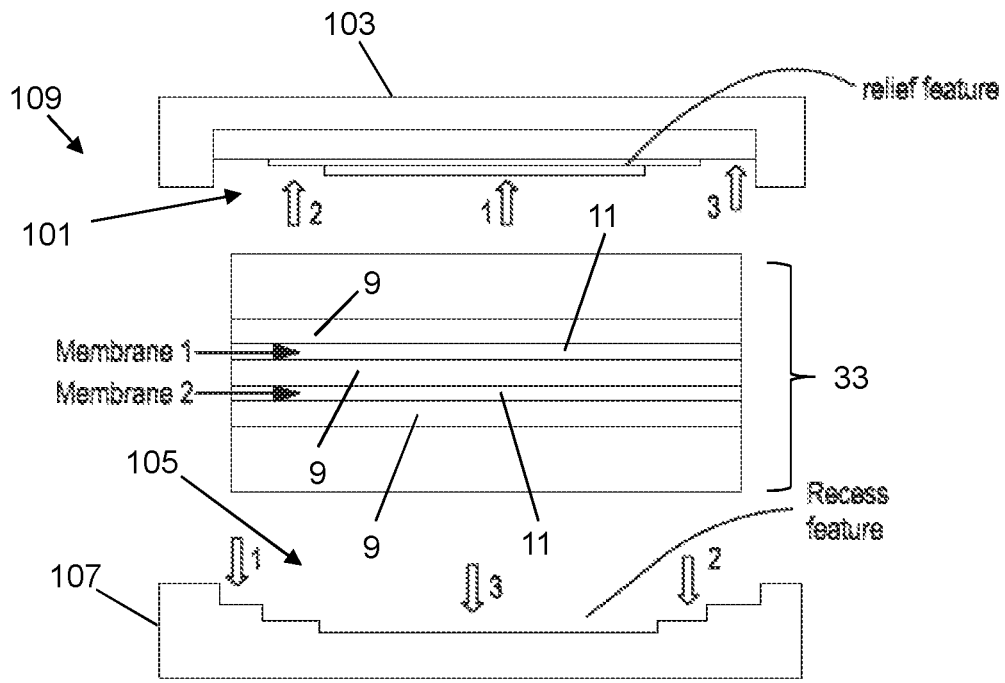
FIG. 13A-13B. Step-and-Recess feature (exaggerated) to provide uniform force over the membranes and corresponding fluid seal (FIG. 13A) and corresponding unwanted deformation and non-uniform pressure without step or recess feature (clamp distortion) (FIG. 13B).
Figure 13B:
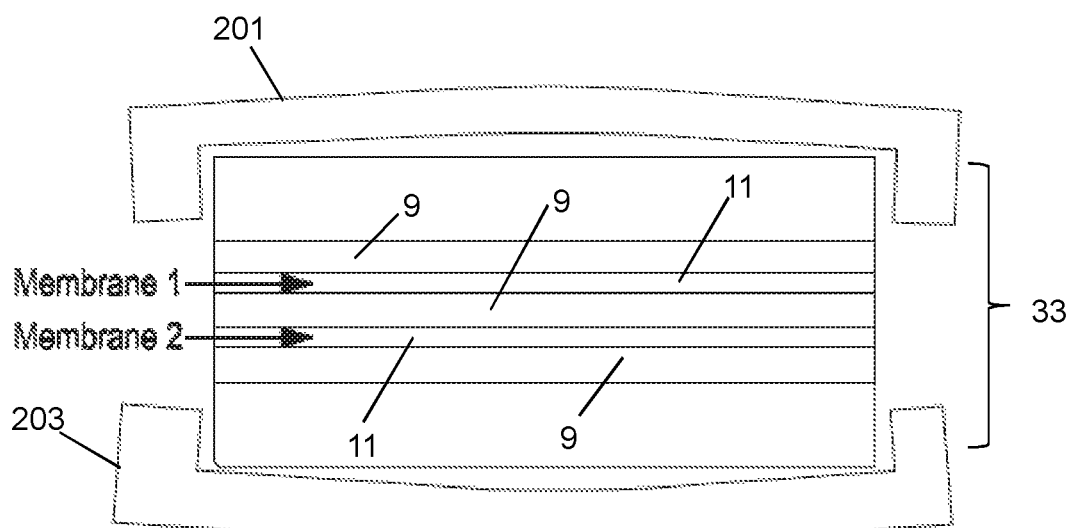

The step feature 101 in the lid 103 and the complimentary recess 105 in the base plates 107 of the clamp 109 are meant to press all areas of the multi-layer bioreactor 33 device in an effort to prevent leakage past the gaskets 9 (compare FIGS. 13A and 13B). In effect during clamping, the multi-layer cartridge of bioreactor 33 is slightly bent because the center part of the lid 103 is pressing the bioreactor 33 device down in the middle (upward arrow labeled "1" in FIG. 13A) first, causing the outer edges (downward arrow labeled "1" in FIG. 13A) of the bioreactor 33 device on the bottom plate 107 to also press first. As the clamp 109 is closed tighter the next step 101 on top presses down a bit further outward (upward arrow labeled "2" in FIG. 13A), and vice-versa, the bottom plate 107 presses more on the same feature (downward arrow labeled "2" in FIG. 13A). The last step to contact the multi-layer bioreactor 33 device is the outer edge (downward arrow labeled "1" in FIG. 13A) which presses down at the same time that the bottom center (downward arrow labeled "1" in FIG. 13A) is contacting. The polycarbonate sheet that the base 107 and lid 103 is made from will bend under the pressure of the clamps 109, so the step 101-and-recess 105 feature takes advantage of this property from the plastic.

As shown in FIG. 13B, without the step 101-and-recess 105 feature, the buckle clamps 109 warp the polycarbonate clamping plates 201 (top) and 203 (bottom) so that there is virtually no pressure on the center of the multi-layer bioreactor 33 device, causing leakage through the gaskets 9 and across channels 7. Any of the devices and methods described in PCT/US2017/061602 are specifically incorporated by reference herein, particularly for the step feature 101 of the buckle clamp 109.

Example 7: Gas Exchanger

FIGS. 14A-14E show various views and cross sections of a gas exchanger 91, useful for combining appropriate levels of $CO_2$, air, oxygen, $N_2$ and other gases of interest, to obtain desired gas compositions.

Figure 17:
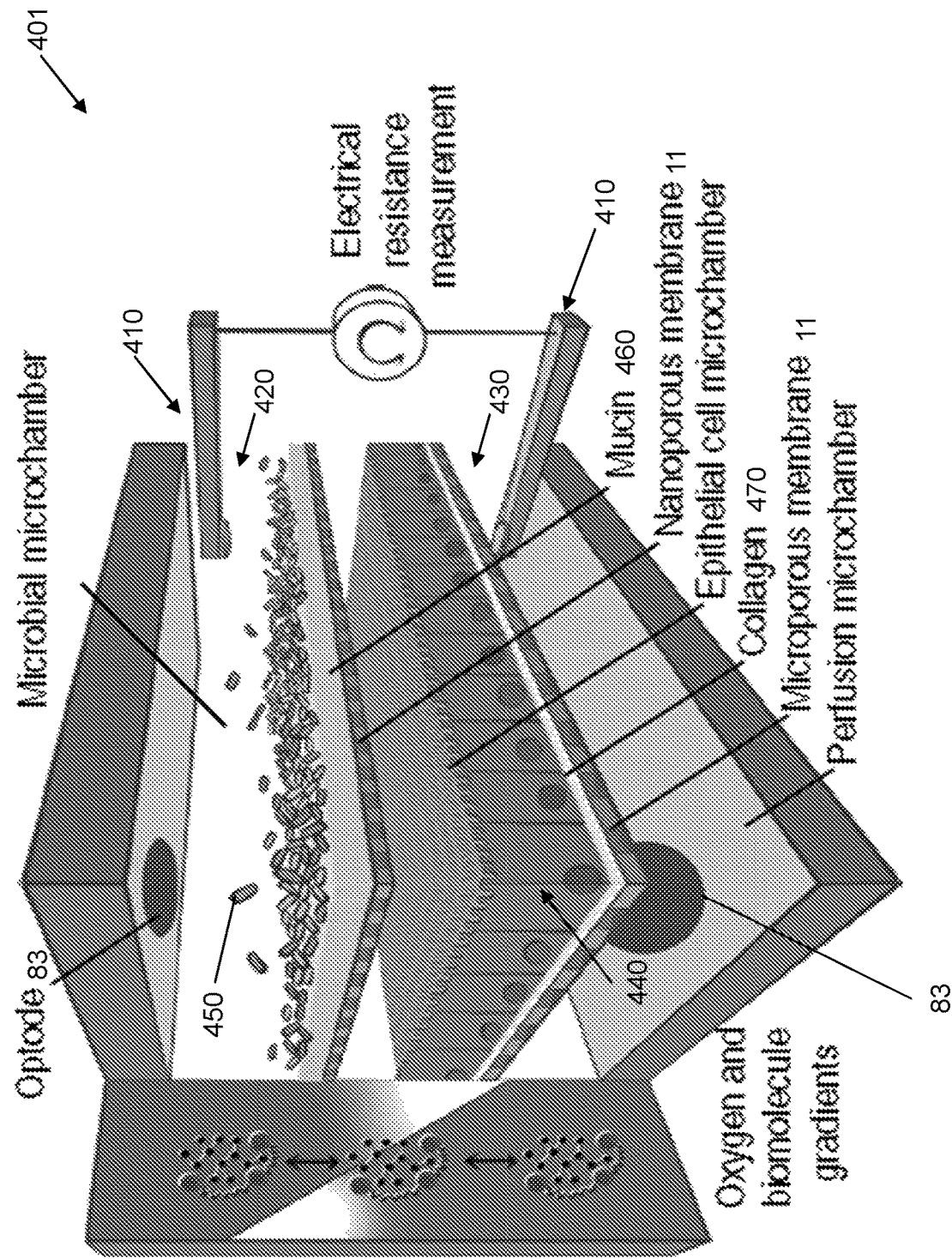
FIG. 17. Schematic diagram of the HuMix—Gut-on-a-chip model.

Example 8: HUMIX 2.0—Human-Centered Design
for Microfluidic Gut-on-a-Chip Integrated Platform.
FIG. 17—HuMix—Gut-on-a-Chip Details The innovative Human-Microbial Cross-Talk (HuMiX) "gut-on-a-chip" model 401 has proven its ability to mimic the human Gastrointestinal (GI) tract [1], [2]. This platform model may serve as a microfluidic model to study irradiation of the human GI tract. The HuMiX microfluidic bioreactor 33 enables co-culture of human intestinal epithelial cells and microbial cells under conditions representative of the GI human-microbe interface. The presence of the microbiome makes this system unique and ideally suited to study radiation effects on the human GI tract, given the growing evidence that radiation-induced dysbiosis promotes susceptibility to radiation-induced injury and intestinal inflammation (e.g. colitis) [3].

The co-culture strategy brings a unique quality feature of the biological analysis performed through the HuMiX model 401. The combination of these biochemical requirements with mechanical design constraints, however, leads to a complex and sensitive set-up that requires expert and special attention from its users. Various upgrades expand the capacities of the platform and the control and monitoring of the cells environment, such as: inclusion of inlaid Ag/AgCl electrodes 410 in the top 420 and bottom 430 microchambers to allow continuous monitoring of transepithelial electrical resistance (TEER) [4] [5] [6], and characterization of oxygen permeation [7] and hypoxia [8]. These upgrades expand the analysis and enrich our understanding of the biology, but also bring more complexity and lead to a more cumbersome set-up, which can make the use of the bioreactor 33 devices a delicate operation. As described below, the assessment of the effect of mission-relevant doses of simulated space radiation on the human GI tract requires, for each quality of radiation, the shipment and irradiation of ten GI tract bioreactor models to a test facility 607. The intensive use of the platform model 401 confirms the need and the positive short-term impact of an easy-to-use, reliable, and parallelizable GI tract model. The designs provided herein are also an important part of an ultimate in-flight application; by designing a human-centered and compact platform, we facilitate the adoption of GI models to in-flight experiments on ISS.

The example is a design of a new generation of HuMiX to facilitate its use and increase its efficiency and reliability. The users 59 (e.g., scientists) and their environment are at the center of the design specifications, during all the different use-cases (including, ultimately, astronauts performing in-flight experiments).

Specific aspects include: Perform a comprehensive Functional Design Specification to guide and evaluate the design improvements; Improve the user 59 experience; Improve adequacy to user 59 environments 601; and Improve efficiency and reliability.

The devices and methods relate to out-of-the-box ideas for incorporating human centered design and improves efficiencies of research that can lead to new countermeasures for high-priority risks to human health in deep space exploration missions." The improved HuMiX design is particularly relevant for spaceflight environment.

A prerequisite to ensure a human-centered guidance of the design process, is to perform a comprehensive Functional Analysis placing the users 59 at the center of the approach. To fit user expectation, the first step is to build a list of the user specifications in a comprehensive manner: considering the different states of use and the associated environments. A dedicated systematic approach is applied [9]-[14] and the users (male/female researchers) have a central role in defining the specifications. The user requirements are translated into design functions, associated with criteria (Boolean and/or value). The resulting Functional Design Specification is used to guide the technical choices at each step of the project. A compliance matrix of the new design to the Functional Design Specification is produced to quantifiably evaluate the new design ability to answer the user-defined specifications. Each design choice and change is submitted for compliance evaluation from the beginning of the project to subsequent prototyping and test steps. This systematic approach facilitates focus on the evaluation of technical solutions and the corresponding environment, and to consider the mechanical and engineering constrains as levers of user satisfaction. Specific attention and high priority is given to the specifications identified as strong factors of user-satisfaction and safety: levers to decrease errors, reduce the learning curve and fatigue, improve ergonomics and tactile feel, and improve perception of the product.

The user experience is evaluated and improved for each state of use of the HuMiX platform model 401 (e.g., as improved for use with bioreactor 33 and system 53 in environment 601).

The systems and methods provided herein address problems associated with conventional systems and methods, including the numerous steps and attendant increase in risk of contamination. The irradiation process is not compatible with having any metallic part on the core design model 401 of bioreactor 33; to address this requirement, an adhesive design and assembly process is used. As shown in FIG. 17, this process involves many steps associated with different conditions: the mucin 460 and collagen 470 coating of the membranes 11 need to be performed in a sterile environment while the final closure requires a hydraulic press to ensure the proper sealing. This complex assembly process takes a great deal of user time and comes with a high risk of contamination: leading to the strong discontent of realizing after several days of work that the entire experiment has failed.

To address this issue, we simplify the core design to minimize the number of parts and the assembly process by improving the adhesive strategy or through another non-metallic fastening strategy (e.g. threads, latches, etc.)

Figure 18:
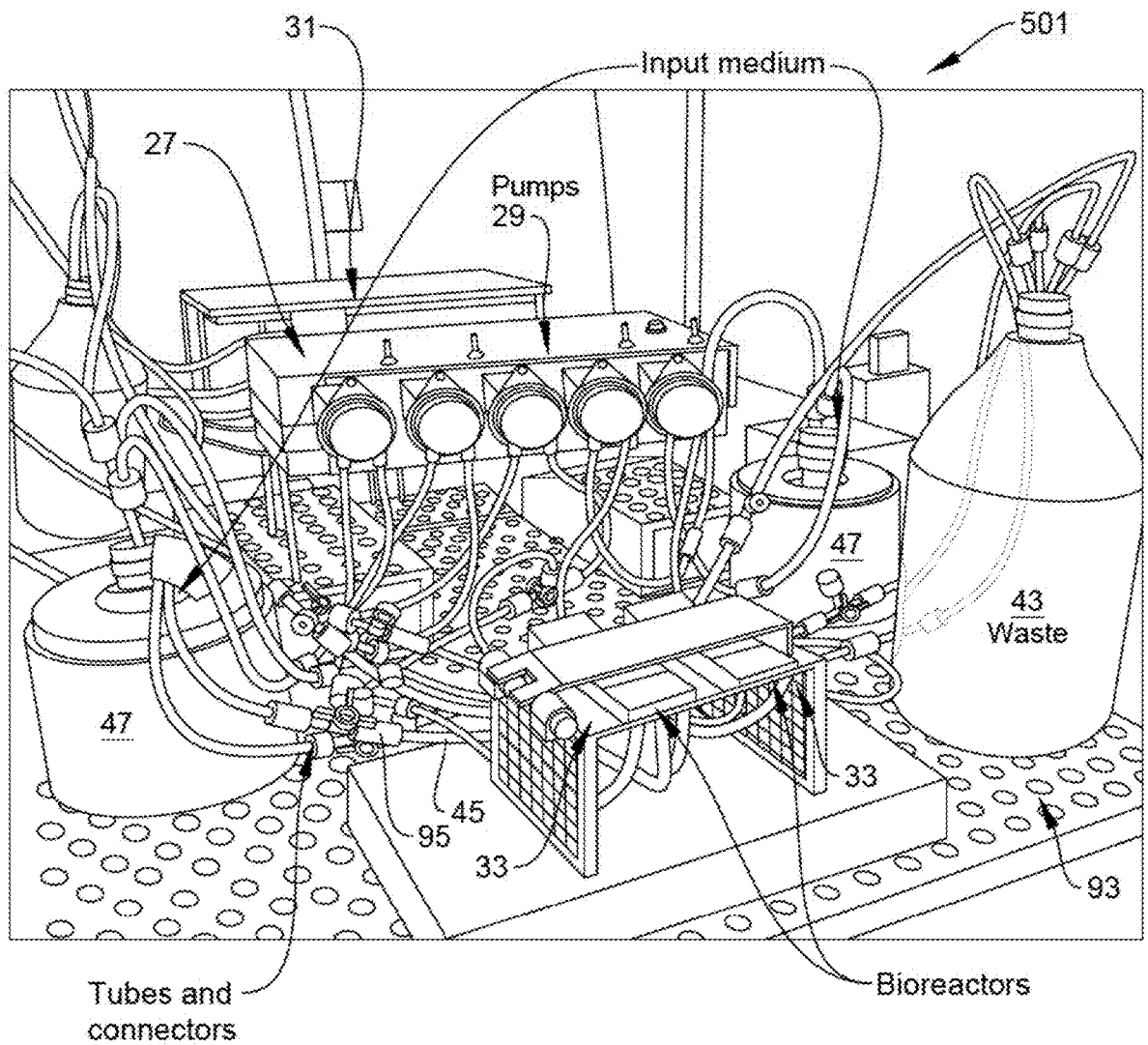
FIG. 18. Current set-up of the HuMiX with two bioreactors.

Set-Up: Certain systems require a relatively large number of steps, including placement and connection of numerous parts and ancillaries, with an attendant high risk of error and contamination. FIG. 18, for example, shows a set-up with two bioreactors. The set-up 501 comprises connecting the input-output of the 3 perfusion chambers to the tubing, pumping system 27, inoculation and sampling connectors, vents, medium 47 and waste 43 bottles. If more monitoring or control is desired for the experiment, the TEER system and nitrogen input may be deployed. Such a set-up can take substantial time and effort, including up to an entire day, and results in a tangle of tubes and ancillaries making it difficult for the user to check proper functionality (FIG. 18). The high number of manual connections also leads to a high risk of contamination and/or involuntary misplacement or unplugging of tubes 45.

Figure 19:
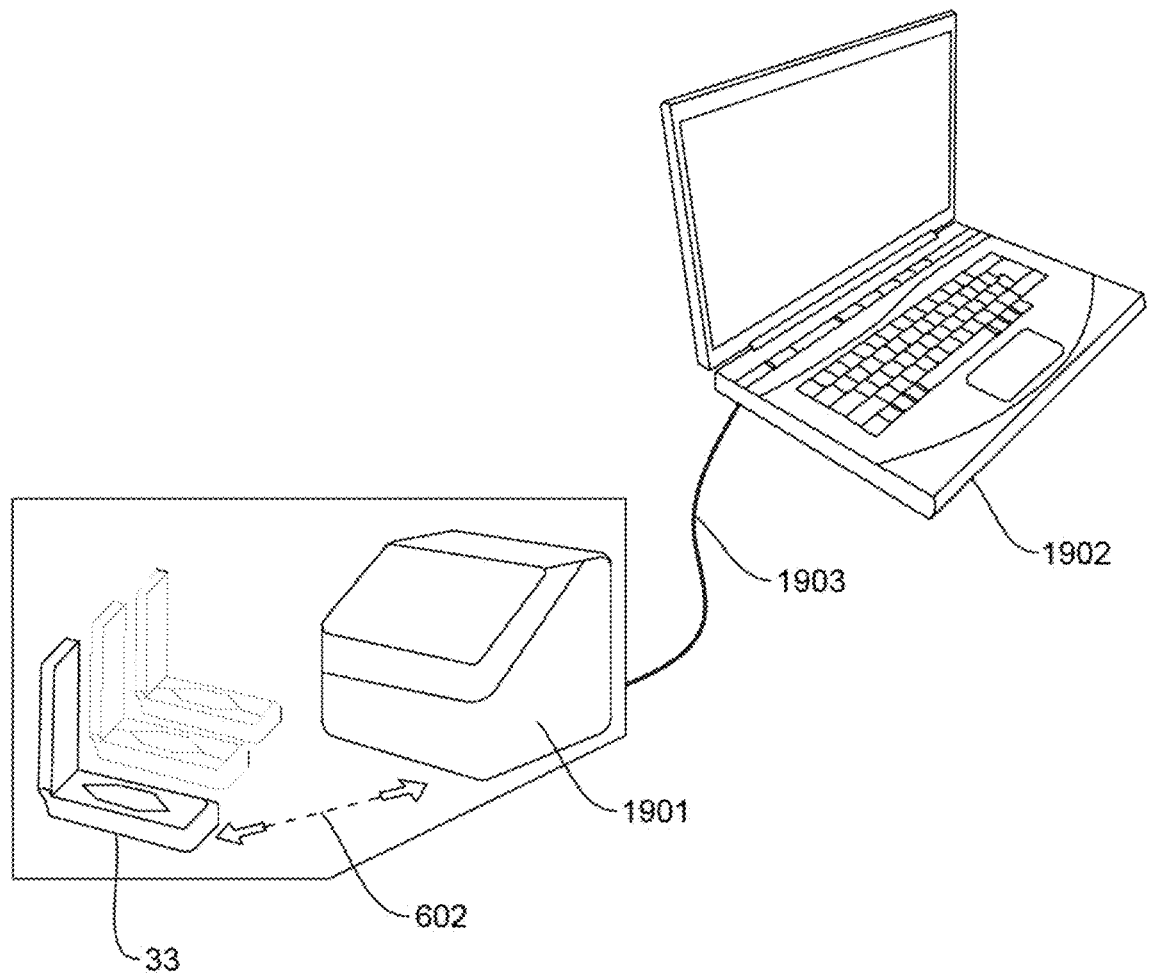
FIG. 19. Human-Factor augmentation of the HuMiX workstation system.

To address this issue, the systems 501 and methods associated with FIG. 18 are, as shown in FIG. 19, configured as an integrated system 1901, comprising the bioreactors 33 (core) and an ancillaries platform that are readily connected in a plug-and-play 602 manner. The end result is a ready-to-use system 1901 having integrated therein necessary tubing 45, pumps 29, media 47 supply and ancillaries onto which the bioreactor(s) 33 are conveniently, reliably and without risk or error or contamination easily connected, such as, using a plug/unplug connection 602 between bioreactors and the integrated system 1901. As desired, integrated system 1901 can be connected to a stand-alone controller, such as a computer 1902, hand-held, or the like, for control and monitoring, via a hard-wire 1903. Although illustrated as separate components, the controller or computer can be integrated into a system 1901. Although illustrated as hard-wired connection, the controller or computer 1902 can be in wireless communication with system 1901. As desired, any one or more bioreactors 33 can be shipped to a remote testing facility. As desired, the integrated system 1901 with bioreactor 33 integrated therein and undergoing tissue culture (including monitoring and/or control) via computer 1902 in wireless connection thereto, can be shipped together to a remote testing facility.

Once the HuMiX system is set-up and primed, three distinct inoculation steps for epithelial cells 440, bacteria 450, and immune cells are needed. For each of these steps, the numerous manual activity by a user is required: move the entire bioreactor assembly from the incubator to the biosafety hood 93, turn-off the flow, inoculate manually with a syringe, move back to the incubator 55, let the inoculated product settle for the proper duration, turn-on the flow. All these steps require time and full attention from the user and carry with them the risk of contamination and/or involuntary misplacement or unplugging of tubes 45. The same steps are needed when sampling the output medium 47. The monitoring capacity is also limited by the complexity of the set-up 501.

To address these issues, we integrate the inoculation and sampling process into an integrated system 1901. The ready-to-use system 1901 consider the inoculation and sampling steps and minimize human manipulation during these steps: automation and/or better connectors and containers for medium fluid 47 and waste 43 (cartridges).

The ability to monitor the proper behavior of the system 53 is also considered for an improved control board 31 adapted for an independent and self-contained embedded system through the integration of sensors 99 (e.g., optodes 83) and visual access.

The firmware for flow regulation is improved and augmented with monitoring functions (e.g., connection to sensors 99 and active control board 31). The software design and data-pre-processing is focused to provide just the necessary amount of control, information and alarms to a user.

The final step of an experiment or culture may require unplugging the bioreactor 33 and opening it to access the cell layer 440 and perform the assays, as needed. This last step is particularly delicate and failing at this step means jeopardizing 8 to 10 days of effort and resources provided by the user. The following issues are often encountered: the bioreactor 33 necessitates a long opening time and an important part, or all the cells, are vulnerable to damage, including death, before an assay can be performed. The mechanical loads and strains during the opening process can damage the cell layer 440. The adhesive assembly can be challenging to take apart, and there is a risk of user injury to address the adhesive assembly, such as inserting a razor blade between the layers to take them apart.

To address this issue, we focus on an easy and safe opening for the user by improving the adhesive properties and designing adequate and safe opening tools, or by changing the assembly strategy (e.g. threads, latches, etc.).

Compactness and Parallelization.

As described, simplifying and minimizing the actions required by a person is a priority. In addition, the space occupied and mass of the system 53 are also important issues. With the set-up 501 illustrated in FIG. 18, an entire incubator 55 is needed to run a maximum of two bioreactor 33 devices, leading to an intricate tangle of tubes 45 and connectors 95. It is thus essential to provide a more integrated and "parallelizable" modular platform, such as system 1901 of FIG. 19.

The integrated system is, therefore, modular and allows for the set-up of one or several bioreactors 33 in a fast and efficient manner. Compactness is achieved, at least in part, by using multiple channel pumps 29 and modular manifolds and connectors 95 to distribute the flowing media 47 in one or several chambers of bioreactors 33, as shown, for example, in FIG. 15. Furthermore, mutualizing the sensors 99 (e.g., $O_2$ 37, pH 39, and TEER 41) and monitoring components between the different bioreactors 33 and reducing the occupied space and global mass of the system 53 further reduces the footprint and increases compactness. Modularity is also an important element in designing the regulation and monitoring software run by control board 31 and/or PC 57.

Compatibility with irradiation and shipment: Conducting the experiments at a test facility adds important constraints to the user 59 and the system 53 design. Regarding the design itself, the absence of metallic parts and the limited thickness of the lids 103 of the bioreactor 33 to allow for cell irradiation while ensuring the user's 59 safety while manipulating the bioreactor 33 in the proper timeline. The user 59 also needs to establish a complex logistics to: set-up and seed the bioreactors 33 one week before irradiation, pack and ship (e.g., via a vehicle 605) the sealed bioreactors 33 to test facility, receive the sealed bioreactors, unseal the bioreactors 33, and restore the perfusion flow, proceed to irradiation, and perform the assays at test facility. All these steps require a definite timeline and must be performed without contamination. These trips can be stressful for the users because any hazards or mistake (late delivery, forgotten component, leak, etc.) can jeopardize the experiments of the entire trip.

The integrated system 1901 addresses these concerns by a platform with ancillaries and bioreactors 33 that easily plugs into and unplugs from the platform. The connection between the bioreactors 33 and the ancillaries platform ensures sealing and minimizes risk of contamination for the sealed bioreactors (e.g., bioreactor 33 of FIG. 19, in a closed-lid or sealed configuration). This dual parts strategy allows the user to set-up a mirror platform at the test facility and avoid the shipment of all the ancillaries for each trip. Only sealed bioreactors are shipped using, for instance, vehicle, thus reducing travel preparation and stress for the users.

The risk of contamination of the bioreactor 33 chamber from its environment is an important aspect and is considered, but the risk of contamination also needs to be addressed from the point of view of user safety. The bioreactor 33 may contain bacteria 450, and bloodborne pathogens during use, from which the user environment must be protected at all times, including for any biohazardous biological or chemical agents.

An important source of dissatisfaction for the user is the lack of reliability: seeing all the efforts and energy deployed for 8 to 10 days leading to an inconclusive result or a scattered cell layer 440 is disheartening. By limiting the risk of contamination, the instant systems and methods provide a more reliable experimental platform, improvement of the general efficiency of the bioreactor and system through a better understanding and control of the cells' chemical and mechanical environment. Numerical simulation (COMSOL) may be used to describe the flow conditions and gas-concentration (mass-transfer) in the bioreactor 33 chamber [15]-[21]. The numerical strategy allows for comparison and improvement in the shape of the bioreactor 33 chambers to achieve a better control of flow and shear stress, while minimizing the number of designs tested. Numerical simulation and correlation to measured data provides, in turn, the guidelines for a more robust and integrated gas-control solution for applying an oxygen gradient representative of in-vivo conditions [22]-[24].

Figure 20:
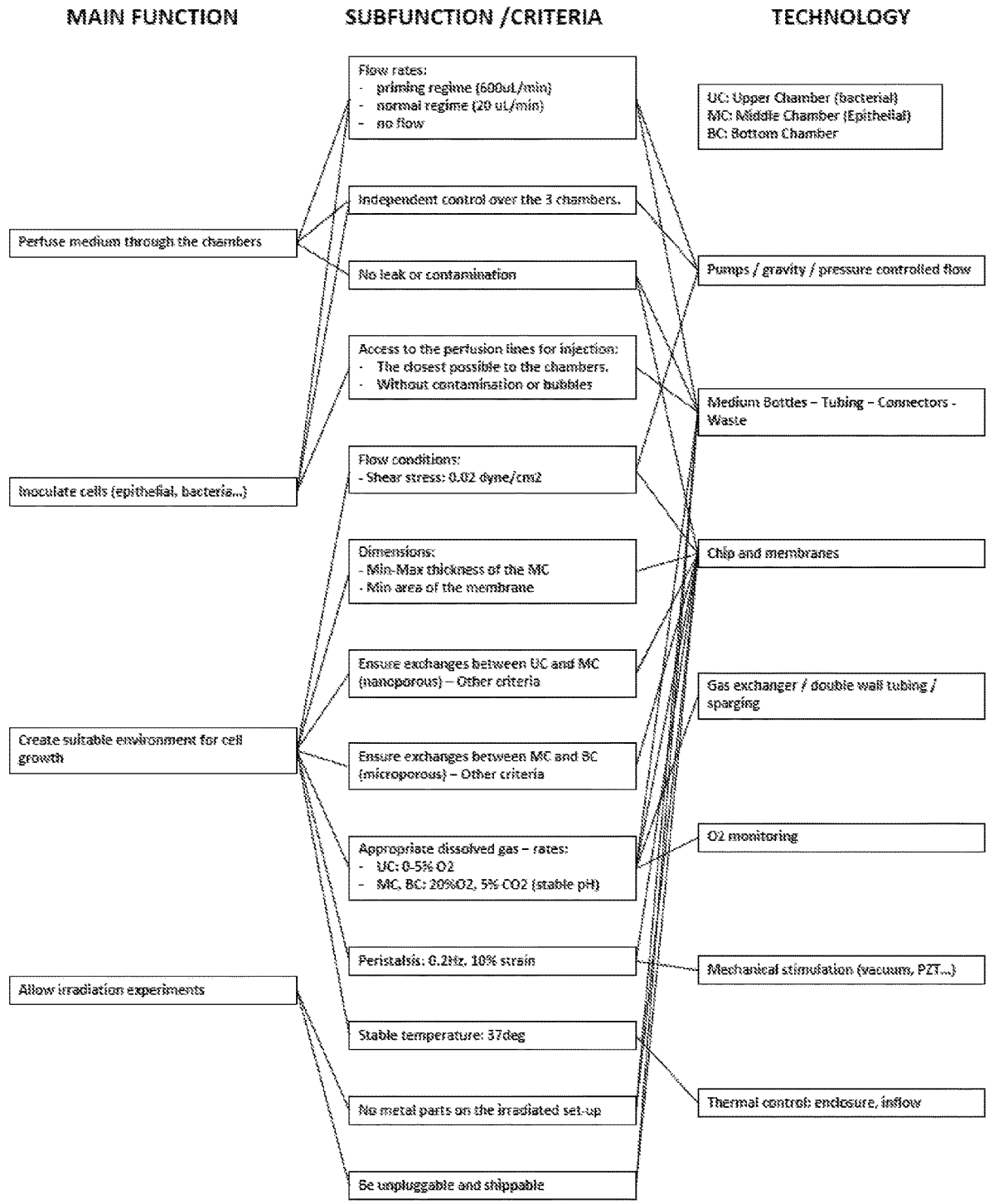
FIG. 20. Flow chart summary of the functions/requirements of the HuMiX workstation and related technological solutions, with exemplary parameter ranges.

FIG. 20 summarizes various functions and requirements of the co-culture device, including the HuMiX device, along with related technical solutions. Any one or more of the descriptors of FIG. 20 may be incorporated into any of the automated cell culture systems described herein, including related culture methods. For example, the HuMiX system has three distinct chambers that is a robust model of an animal gut, and is also generally described as a "Gut-on-Chip" system. As shown in FIG. 17, the three chambers facilitates co-culture of bacteria cells, epithelial cells and immune cells, with an independently controllable perfusion microchamber, microbial microchamber and epithelial (animal) microchamber. Each of the microchambers are independently controllable in terms of composition (e.g., bacteria have different requirements from epithelial cells) and flow-rate.

Figure 21:
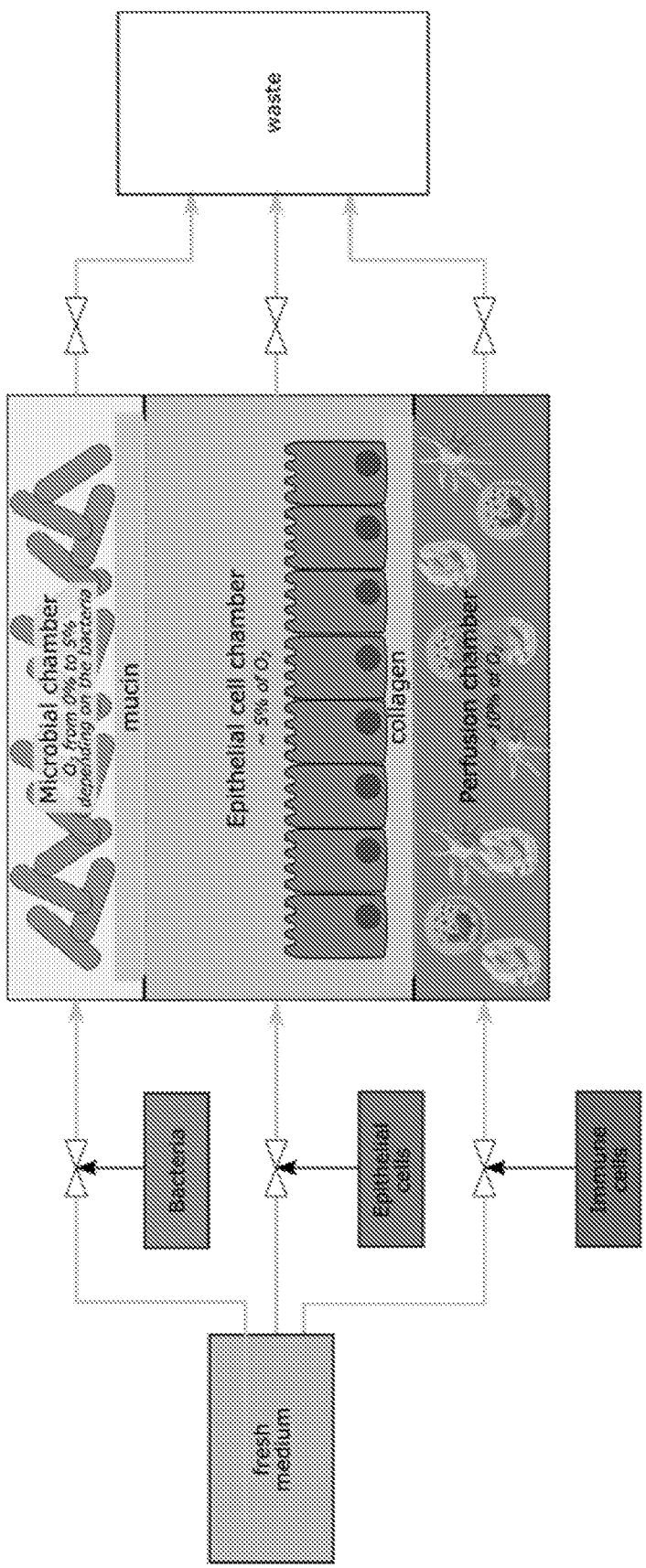
FIG. 21. Schematic of main components of a three-microchamber system for co-culture of two cell types (e.g., bacteria, epithelial) and a dedicated perfusion chamber.

In this manner, medium is perfused through the three chambers, and there can be communication between chambers 1-2 (microbial-epithelial) and 2-3 (epithelial and perfusion), as shown in FIG. 21. The perfusion chamber may contain immune cells. In this manner, the systems is a convenient platform for inoculation of epithelial cells. The systems also facilitate possible co-culture with inoculated bacteria and immune cells. The systems also facilitate establishing an oxygen gradient, with FIG. 21 exemplifying 0-5% $O_2$ in the microbial chamber, about 5% $O_2$ in the epithelial cell chamber, and about 10% $O_2$ in the perfusion chamber. The systems is also compatible with additional layers/chambers and can be made of an elastomeric material to model peristaltism, where changes in pressure result in deformations of the layers and corresponding stresses on the cells supported by the layers, in a relaxation/contraction type cycle.

Gas control of $O_2$ and $CO_2$ can be achieved by having dedicated inlet gas lines of $O_2$ and $CO_2$. Any of the gas lines may comprise gas-permeable flow lines to facilitate controlled diffusion into an adjacent microchabmer.

Figure 22:
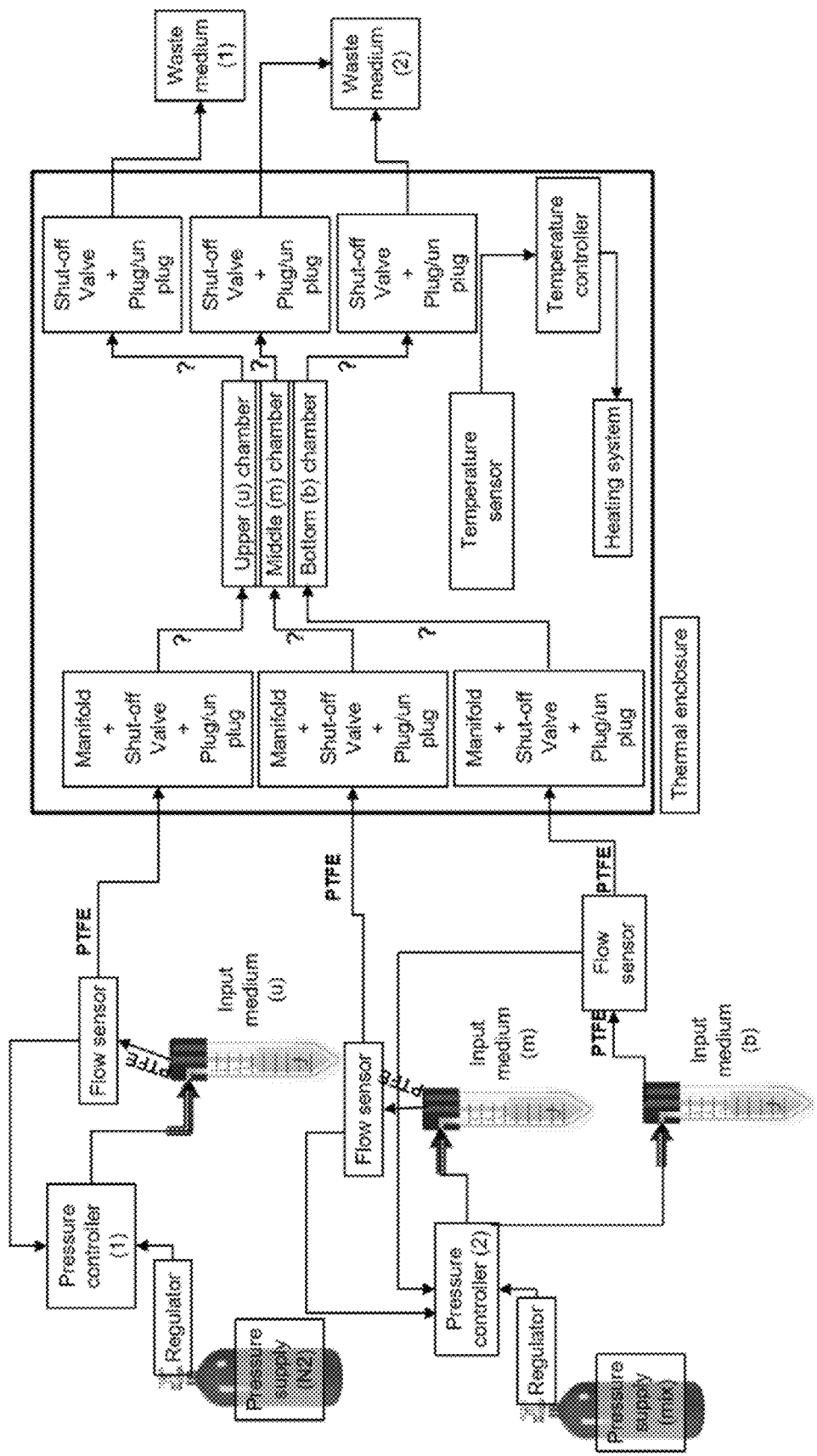
FIG. 22. Schematic illustration of components useful for a pressure-driven perfusion system.

As illustrated in FIG. 22, the system may rely on pressure-driven perfusion. The devices described herein may, therefore, further comprise various controllers, sensors, manifolds, valves and other components relevant for control of pressure and flow. The device may have flow shut-offs to facilitate unplugging of the device. The device may allow inoculation (without bubbles) and have no empty space. Metal is preferably avoided, with the systems being air-tight to minimize unwanted contamination. Accordingly, tubing selection is important with relevant ports and fittings. Options include PTFE tubing, stop-cocks and microfluidic adapters. Of course, the system may be more fully automated, with electronically controlled valves, regulators and the like, whose functionality may be controlled by signals received from one or more sensors, including outside the thermal enclosure and/or inside the thermal enclosure.

The devices and systems provided herein are compatible with pneumatic control of medium flow. Such control serves two functions, namely flow control (and attendant shear stress in the microchambers) and dissolved gas concentration. The flow-rates span from no-flow, to a normal flow range (e.g., 1 µL/min to 1 mL/min, and any sub-ranges thereof, including about 20 µL/min) and a higher "priming" flow (e.g., greater than 20 µL/min). The system should not have bubbles and can achieve up to a desired gas saturation.

The devices and systems may be configured to model peristalsis, where there is a mechanical deformation. Typical deformations are at a frequency of, for example, 0.15 to 0.2 Hz and an amplitude of about 10% strain (e.g., from dimension (e.g., diameter) of L to L+0.1 L, with a period of about 5 to 7 seconds.

A variety of oxygen permeation tests are performed to, for example, select appropriate tube or channel compositions, pumps, connector (e.g., barbs), stop-cock and the like.

Example 9: Gas Enclosure and Holder for Culture Media Having Controlled Gas Concentration Any of the devices and methods may further comprise specially configured holder 2300 and/or gas enclosures 2400 to facilitate reliable and well-controlled gas concentration level in a media that is introduced to the bioreactor. In this manner, the number of separate fluid channels in the bioreactor may be reduced, without sacrificing the ability to control gas concentration levels in the bioreactor.

Figure 23A:
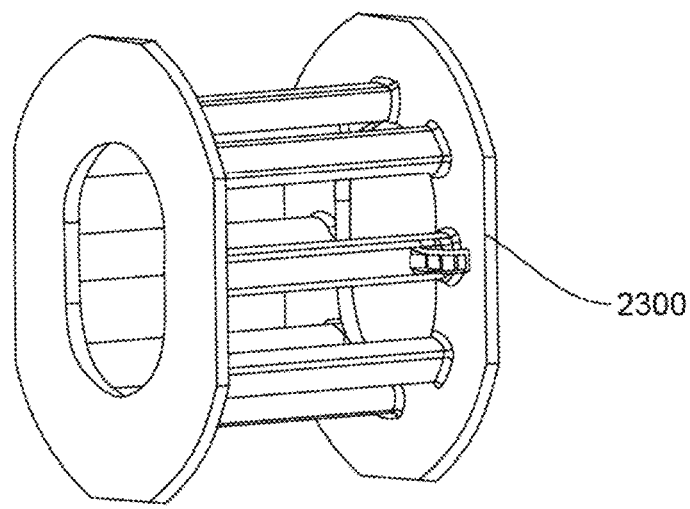
FIG. 23A-23B illustrate a holder with tubing in a reeled-up configuration.
Figure 23B:
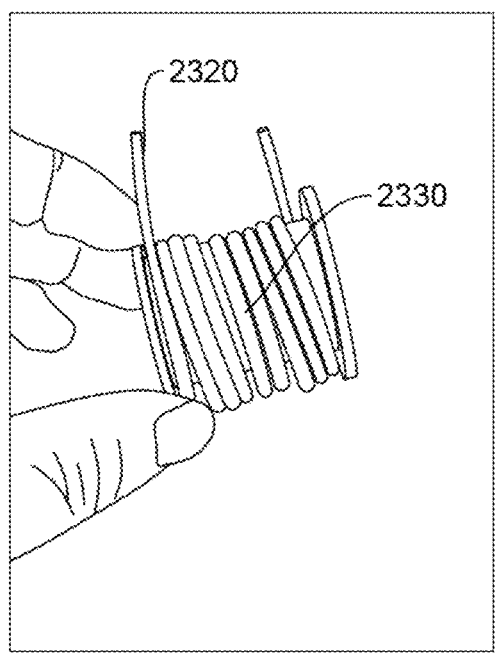
Figure 24A:
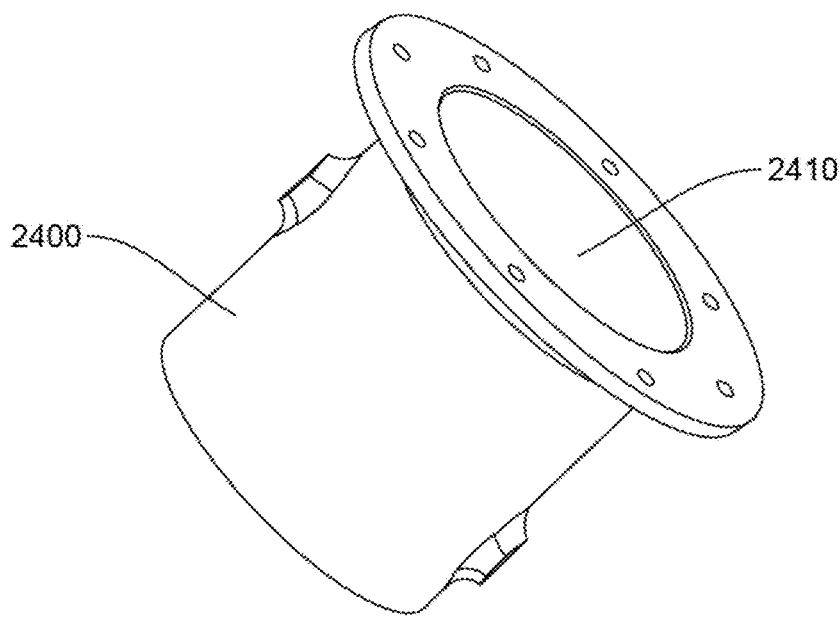
FIGS. 24A-24D illustrate holder (FIG. 24A), lid (FIG. 24B) and assembled system (FIGS. 24C-24D).
Figure 24B:
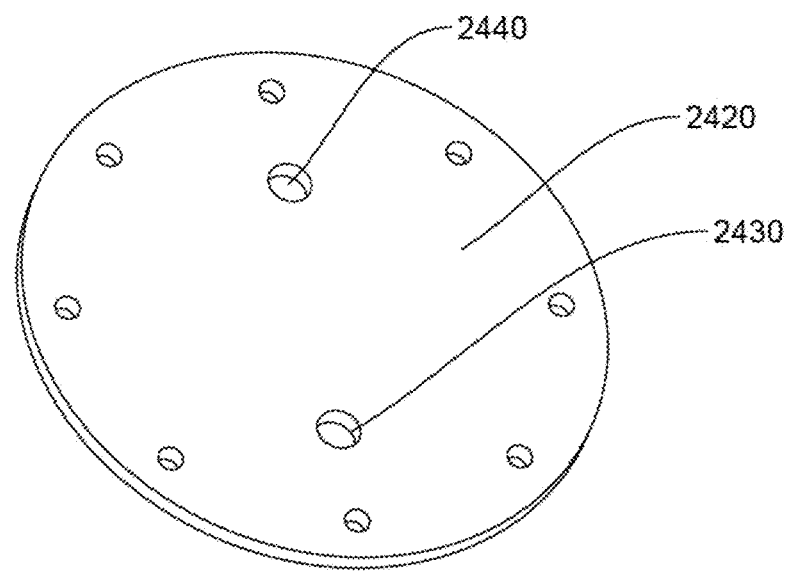
Figure 24C:
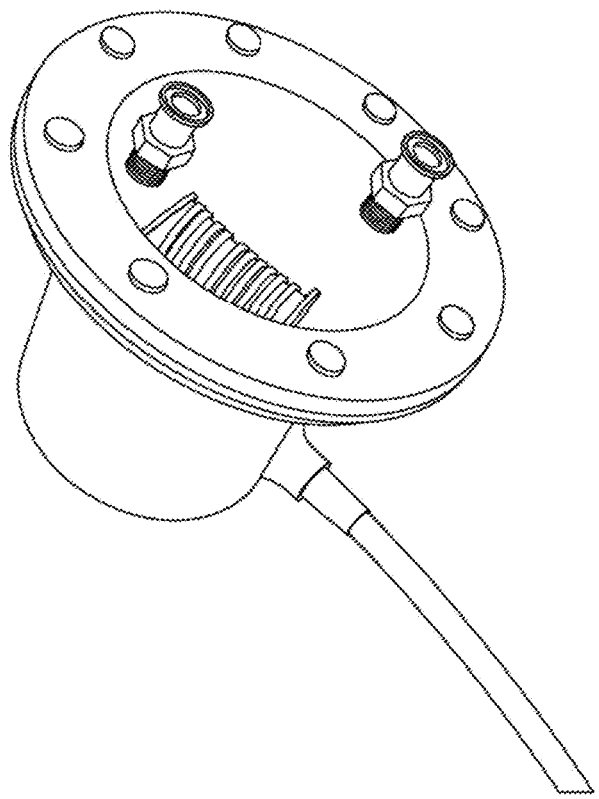
Figure 24D:
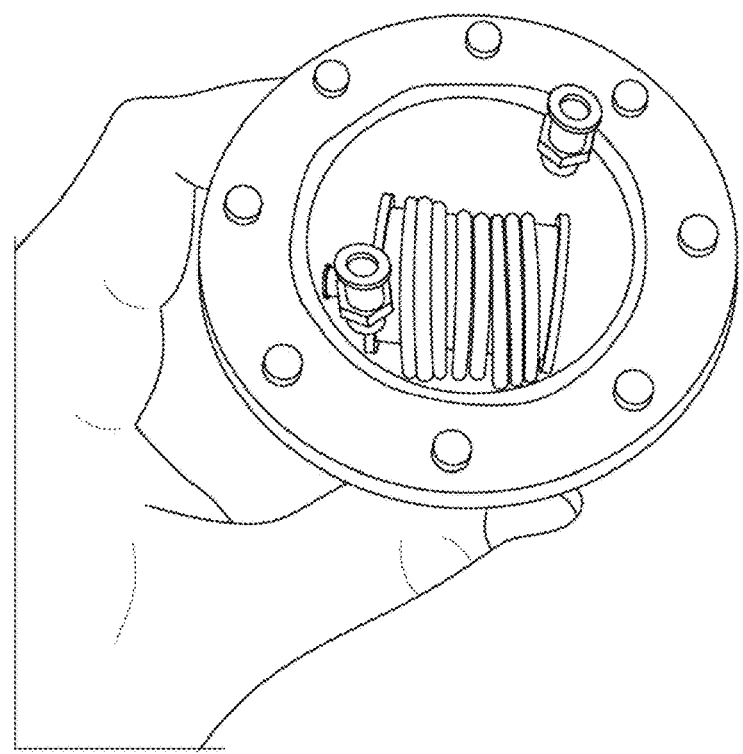

FIGS. 23A-23B illustrate a holder 2300 configured to hold a gas permeable tube 2320 in a reeled-up geometry 2330. The gas permeable tube is connected to a bioreactor fluid port. A gas chamber 2400 having an enclosure 2410 configured to contain the holder within the enclosure. In this manner, a very well-controlled gas exchange between the gas chamber and a lumen of the gas permeable tube is achieved. The gas chamber may be air-tight secured with a chamber lid 2420 having ports 2430 2440 and passages to accommodate fasteners for air-tight connection, thereby allowing for controlled gas concentration in the enclosure, and corresponding diffusion into lumen containing fluid media for subsequent introduction to a bioreactor.

In this manner, cell culture gas inflow may comprise passing culture gas through the gas exchanger device illustrated in FIGS. 23A-24D. An advantage of such a cell culture gas inflow configuration is that risk of unwanted contamination is reduced. For example, any of the methods may further comprise the step of sterilizing the holder with reeled-up gas permeable tube, including by autoclaving. The tube may contain the media that together is autoclaved. To ensure air-tight connections, a holder gasket may be positioned between the holder 2400 and lid 2420, as shown in the assembled device of FIGS. 24C-24D, having lid, holder, fasteners, passages to provide desired gas concentration in the enclosure (and thereby, desired gas concentration of media in the lumen of the tube).

FIG. 25 illustrates various factors for selecting tubing composition, length and geometry, such as wall thickness and lumen diameter, as all those factors influence gas exchange and loss.

This example demonstrates a platform that minimizes contamination risks as the media remains in tubing, including autoclavable-compatible tubing (Silastic-508-007, for example). There is no contact with moving parts and gas is not sparged into the media, but rather permeates through the tube wall via the specially-configured holder and enclosure, all of which are autoclavable. The system also avoids having to use a membrane, thereby minimizing risk of leaks.

REFERENCES

[1] P. Shah et al., "A microfluidics-based in vitro model of the gastrointestinal human-microbe interface," Nat. Commun., vol. 7, pp. 11535-, May 2016.
[2] M. M. G. Eain, J. Baginska, K. Greenhalgh, J. V. Fritz, F. Zenhausern, and P. Wilmes, "Engineering Solutions for Representative Models of the Gastrointestinal Human-Microbe Interface," Engineering, vol. 3, no. 1, pp. 60-65, 2017.

[3] H. Sokol and T. E. Adolph, "The microbiota: an underestimated actor in radiation-induced lesions?," Gut, vol. 67, no. 1, p. 1, January 2018.

[4] C. J. L. Daniel H. Elbrecht and J. J. Hickman, "Transepithelial/endothelial Electrical Resistance (TEER) theory and applications for microfluidic body-on-a-chip devices," J. Rare Dis. Res. Treat., vol. 1(3), pp. 46-52, 2016.

[5] B. M. Maoz et al., "Organs-on-Chips with combined multi-electrode array and transepithelial electrical resistance measurement capabilities," Lab Chip, vol. 17, no. 13, pp. 2294-2302, 2017.

[6] O. Y. F. Henry, R. Villenave, M. J. Cronce, W. D. Leineweber, M. A. Benz, and D. E. Ingber, "Organs-on-chips with integrated electrodes for trans-epithelial electrical resistance (TEER) measurements of human epithelial barrier function," Lab Chip, vol. 17, no. 13, pp. 2264-2271, 2017.

[7] S. C. Lesher-Perez et al., "Dispersible oxygen microsensors map oxygen gradients in three-dimensional cell cultures," Biomater Sci, vol. 5, no. 10, pp. 2106-2113, 2017.

[8] F. S. M. Busek S. Grunzner, T. Steege, C. Steinfelder, F. Schmieder, U. Klotzbach, "Microfluidic system for in-vitro hypoxia assays," Proc. SPIE, vol. 10061, pp. 10061-10061-10, 2017.

[9] J. Hoyos-Ruiz, J. F. Martinez-Cadavid, G. Osorio-Gómez, and R. Mejía-Gutiérrez, "Implementation of ergonomic aspects throughout the engineering design process: Human-Artefact-Context analysis," Int. J. Interact. Des. Manuf. IJIDeM, vol. 11, no. 2, pp. 263-277, 2017.

[10] N. Karwowski W. Soares, M. Stanton, Human Factors and Ergonomics in Consumer Product Design. CRC Press, 2011.

[11] M. Maguire, "Methods to support human-centered design," Int. J. Hum.-Comput. Stud., vol. 55, no. 4, pp. 587-634, 2001.

[12] D. Norman, The design of everyday things: Revised and expanded edition. Constellation, 2013.

[13] C. D. Wickens, J. G. Hollands, S. Banbury, and R. Parasuraman, Engineering psychology & human performance. Psychology Press, 2015.

[14] S. E. Karl Ulrich, Product Design and Development. McGraw-Hill Education, 2004.

[15] S. Schuerlein et al., "A versatile modular bioreactor platform for Tissue Engineering," Biotechnol. J., vol. 12, no. 2, pp. 1600326-, August 2016.

[16] Y. Tanaka, M. Yamato, T. Okano, T. Kitamori, and K. Sato, "Evaluation of effects of shear stress on hepatocytes by a microchip-based system," Meas. Sci. Technol., vol. 17, no. 12, pp. 3167-, 2006.

[17] D. Egger, M. Fischer, A. Clementi, V. Ribitsch, J. Hansmann, and C. Kasper, "Development and Characterization of a Parallelizable Perfusion Bioreactor for 3D Cell Culture," Bioengineering, vol. 4, no. 2, p. 51, 2017.

[18] A. A. Adebiyi, M. E. Taslim, and K. D. Crawford, "The use of computational fluid dynamic models for the optimization of cell seeding processes," Biomaterials, vol. 32, no. 34, pp. 8753-8770, 2011.

[19] B. Bilgen and G. A. Barabino, "Modeling of bioreactor hydrodynamic environment and its effects on tissue growth," Methods Mol. Biol., vol. 868, pp. 237-255, 2012.

[20] M. M. Nava, M. T. Raimondi, and R. Pietrabissa, "A multiphysics 3D model of tissue growth under interstitial perfusion in a tissue-engineering bioreactor," Biomech. Model. Mechanobiol., vol. 12, no. 6, pp. 1169-1179, 2013.

[21] P. Yu, T. S. Lee, Y. Zeng, and H. T. Low, "A 3D analysis of oxygen transfer in a low-cost micro-bioreactor for animal cell suspension culture," Comput. Methods Programs Biomed., vol. 85, no. 1, pp. 59-68, 2007.

[22] toru Takahashi, "Flow Behavior of Digesta and the Absorption of Nutrients in the Gastrointestine," J. Nutr. Sci. Vitaminol. (Tokyo), vol. 57, no. 4, pp. 265-273, 2011.

[23] R. G. Lentle and P. W. M. Janssen, "Physical characteristics of digesta and their influence on flow and mixing in the mammalian intestine: a review," J. Comp. Physiol. B, vol. 178, no. 6, pp. 673-690, 2008.

[24] J. Cremer, M. Arnoldini, and T. Hwa, "Effect of water flow and chemical environment on microbiota growth and composition in the human colon," Proc Natl Acad Sci USA, p., June 2017.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a flow rate, temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Tables

TABLE 1

Technical Specification

| Specification/ Function | Comments |
|---|---|
| General | System to hold up to 100 HuMiX bioreactors. 1 bioreactor = 1 HuMiX Bioreactors to be run in sets. 1 set = 4 bioreactors (25 × 4). Bioreactors within a set can be run in parallel (or in series). Sets are independent of one another. Independent peristaltic pump supplying media to the microchannels/chambers of each bioreactor and within each set. Microchannel/chamber dimensions: 200 mm × 4 mm × 0.5 mm Volume: 400 µL Flow Rate of cell growth media to microchannel/chamber: 25 µL/min Current pump system: 3 independently controlled Welco WPM2-P1EA-NGP miniature peristaltic pumps Independent control of each peristaltic pump for each microfluidic chamber of the bioreactor. |
| Environment | Modules to be housed/maintained under the following conditions: 37° C. (±0.1° C.) 5% CO2 (±0.1%) 95% rh Individual Bioreactors (or in sets) to be run as aerobic or anaerobic (<5% O2). Real-time monitoring of % O2 levels in each microfluidic chamber of the bioreactor and incorporate this feedback to maintain set aerobic/anaerobic conditions (adjust N2 levels etc. to maintain an anaerobic environment) within a bioreactor device. Option to supply cell growth media both independently to bioreactor sets and to multiple bioreactor sets from the same feed. o Currently, one bioreactor, where media is supplied constantly to two channels for 7 days, uses approximately 0.51 L of cell growth media. Refill cell growth media aseptically. Cell growth media is maintained at the same conditions, listed above, as the bioreactor or at the module level. Sterile environment maintained within bioreactors/channels prior to loading cells prohibiting any contamination. Source medium remains sterile throughout entire experiment. |
| Gases | Standard aerobic/anaerobic cell culture conditions must be delivered to the system using typical gases (e.g. N2, O2, CO2, air . . .) or possibly collect generated volatiles (e.g. ammonium based compounds) |
| Bioreactor Inoculation, sampling and extraction | Cell inoculation and sample extraction systems should be as hands off as possible for the operator. Inoculation environment: can be either aerobic or anaerobic. Inoculation (e.g. epithelial cells) occurs such that sterile conditions are maintained prior to inoculation of bacteria. Routine sampling of liquid media from the individual microchambers/channels within bioreactors in a set. Liquid samples must be stored in an environment that will allow for subsequent biomolecular analysis (e.g. omics). |
| Power | Power supply: 100-240 VAC 50-60 Hz; Instrument must have an internal battery supply or equivalent alternative power source in the event of external power failure |

TABLE 1-continued

Technical Specification

| Specification/Function | Comments |
| --- | --- |
| Networking Capability | The system to connect to a local network via a RJ45 connection and have a USB port (TBC) for data storage and connectivity to allow the transfer of data from the system. |
| Quantity | 2 systems are provided |
| Documentation | The system delivery includes full design documentation to allow the product to be manufactured by DFM or third parties. |
| Health and Safety | 1. System complies with the appropriate CE, UL and EMC safety standards.<br>2. Instrument able to withstand water splash and suitable for accommodating some biohazard waste. |
| Weight | The overall weight of the system in the range of standard lab automation equipment but no greater than 1800 lbs (std freight elevator) |
| Operating System | MS Windows 10 compatible |

Instrument Performance

| Specification/Function | Comments |
| --- | --- |
| Liquid Flow Rate | Ability to control cell culture medium flow at a particular rate that can be independently varied between each microchamber of a bioreactor and at each microchamber within a range of values (e.g., 5-65 μL/min). |
| Liquid Volume | Instrument maintains constant, uninterrupted (no air bubble introduction) flow of sterile medium over several days (7-10 days) at a minimum flow rate of 25 μL/min. |
| Sampling Ports | Valves up and downstream of each channel allow collection of fluid samples aseptically and can also be used to block the channel flow completely. |
| Sample success rates | 99.9% of human fecal samples comprising multiple bacteria populations will result in a full fingerprint (A full fingerprint constitutes a comprehensive omics analysis accordingly to the methods and protocols described in reference: DOI: 10.1038/ncomms11535 - Shah et al. "A microfluidics-based in vitro model of the gastrointestinal human-microbe interface." Nat. Comm. 7 11535 (2016)), specifically incorporated by reference herein. |
| Integration | All core processes (Sample Preparation/Cells Co-culture) are enclosed and integrated within a single system. |
| Run time | Within one bioreactor, processing time from sample input, including sample prep, to the generation of a fingerprint is carried out in 7-10 days. |
| Footprint | The overall footprint of a bioreactor is no greater than 65 mm × 65 mm × 13 mm, while the overall system is suitable for installation in a standard 8 ft by 4 ft bench space of a laboratory. |
| Contamination free | All non-disposable elements are easily, rapidly (<1 hr) and thoroughly decontaminated between operations. |
| Environmental stability | Operational within a normal room and laboratory environment (15-30° C.) with fluctuating temperature, humidity (10-70%). |

TABLE 3

Loading Instrument

| Specification/Function | Comments |
| --- | --- |
| Bioreactor or set of bioreactors, pre-assembly | Sterile preparation and connection of all components. All components in contact with cell environment (e.g., medium, tubing, connectors, gaskets, etc.) remain sterile throughout assembly of components and loading onto the instrument. |
| Sample preparation/loading | Allow easy, rapid loading of components. Plug and play type operation. |

TABLE 4

Sensor Controls

| Specification/Function | Comments |
| --- | --- |
| TEER | Monitor TEER via integrated electrodes (e.g. e-beam evaporated electrodes onto plastic substrate materials) |
| $O_2$ % | Measure $O_2$ % on input and output of all three channels of a single bioreactor with accuracy of ±2% |
| % rh | Monitor % rh within the system |
| pH | Monitor pH of all three microfluidic chambers for closed-loop control of pH within each bioreactor |

TABLE 5

Instrument

| Specification/Function | Comments |
| --- | --- |
| Controls | 1. Pumps are independent and configurable separately with variable operation start/end times<br>2. Configurable while operating<br>3. Platform or containment system for the bioreactor to keep the instrument from contamination<br>4. Operate pumps with calibrated flow rates between 5 μL/m to 65 μL/m<br>5. Operator controlled operation for bioreactor priming (>500 μL/m) |
| Plug and Play Operation | Modules (4 instruments) are able to be installed and removed without interruption to the system or other operations and be able to be recognized by the control system automatically. |
| Technical and Scientific Functionality | 1. Instrument is configurable and updatable by a technical user<br>2. Interface with a software/program for programming and monitoring status |

TABLE 6

Bioreactor

| Specification/Function | Comments |
| --- | --- |
| Bioreactor Size | The overall footprint of the bioreactor is less than or equal to 65 mm × 65 mm × 13 mm |
| Layout | Two of the three microfluidic channels are fed regular cell culture medium, while bacteria channel requires the capability to achieve anoxic medium |
| Disposable/Single use | The bioreactor is single use integrated and disposable. Semi-flexible design to enable expansion. |
| Outer Shell or containment vessel | 1. Bioreactor shell is a removable outer shell, with port access to the fluidic channels.<br>2. All layers are of a material compatible with |

TABLE 6-continued

Bioreactor

| Specification/Function | Comments |
|---|---|
| | healthy cellular growth (e.g. plastics) and possibly be optically transparent.<br>3. Space or access for optical sensors for O2 % detection and pH monitoring<br>4. Leak proof<br>5. Port access is a compatible common tube connector type (i.e., Barb, NPT, etc.)<br>6. Desirable access for microscopic imaging or visual inspection within the middle microfluidic chamber. |
| Inner Layers (Channels) | 1. 3-layer initial design expandable to multi-layer system<br>2. Formed of a semi-compressible material<br>3. Compatible for healthy cellular growth<br>4. Stackable with <10% misalignment<br>5. Compatible with 2-sided adhesive or a reasonable form of adhesion for the membranes |
| Membranes | 1. Used to separate the channels for cellular/bacterial interaction<br>2. Covers each channel completely<br>3. Bonds to the channel formation with >2 psi strength.<br>4. Prevents cellular/bacterial precipitation to other channels |
| Quick access | 1. Bioreactors able to be dismantled quickly (i.e., membrane access <1 minute disassembly)<br>2. Cellular channel accessible for sampling after disassembly (i.e., cellular membrane removable for microscopy) |
| Ports | 1. Bioreactors contain leak-proof ports for channel/liquid flow and gas impermeable.<br>2. Designed for Barbs/NPT or other connector type that is size/handling compatible. |
| Reagents | Preferably, bio-reagents are pre-loaded automatically in the bioreactor (e.g. cell seeding, media, etc.) |
| Contamination free | No residual decontamination agents remain in the module following any maintenance |
| Documentation | The Bioreactor design should have complete documentation to allow the Bioreactors to be scaled up for future manufacturing by DFM or third party |

TABLE 7

Reagents/Consumables

| Specification/Function | Comments |
|---|---|
| Storage | All reagents required must be stored within the system 4° C. degrees or room temperature |
| Stability | 30 days after loading |
| Consumable Costs | The cost profile for the total bioreactor cost and reagents must be aligned to the cost outlined in the business plan. Costs must include assembly, sealing and packaging for volumes up to 10,000 units/year. |

TABLE 8

Electronics

| Specification/Function | Comments |
|---|---|
| Instrument | All electronics required to support a single Bioreactor:<br>1. Pump drivers<br>2. Sensors (O2, TEER, pH, etc.) and their drivers<br>3. Communications with host PC |

TABLE 8-continued

Electronics

| Specification/Function | Comments |
|---|---|
| | 4. Limited local operator controls and indicators for setup and clean-up<br>5. Accept consumables |
| Incubator | All electronics required to maintain internal environment and to support a number of bioreactors:<br>1. Atmosphere temperature control<br>2. Atmosphere control (O2, CO2, N2, H2O)<br>3. Communications - Host PC to:<br>   a. User<br>   b. Each instrument<br>   c. Incubator<br>   d. Network<br>4. Provide power to instruments<br>5. Provide consumables to instruments<br>6. Accept waste from instruments |
| Power Supply | All electronics required to support system operation<br>1. Provide conditioned power to<br>   a. Host PC<br>   b. Incubator<br>   c. Instruments<br>2. Full Operation (utility power)<br>3. Uninterruptable operation (Battery)<br>   a. Host PC<br>   b. Internal communications<br>   c. Incubator sensors<br>   d. Limited instrument operation |
| Host PC | All electronics required to support operation of the Host PC and required peripherals.<br>1. Monitor consumable and waste levels<br>2. Accepts uninterrupted power<br>3. Provides internal communications with instruments, incubator, gas-and-media distribution<br>4. Provides external communications<br>   a. Local controls and indicators<br>   b. Warning and alarm outputs |
| System | All electronics required to support all instruments, Incubator, Host PC, web interface,<br>1. Accepts consumables (growth media, O2, CO2, N2, and H2O)<br>2. Accepts power:<br>   a. 100-250 VAC, 50-60 Hz (400 Hz optional)<br>   b. 12-24 VDC battery connection for uninterrupted operation<br>3. Accepts wastes from instruments<br>4. Provides consumables to Instruments<br>5. Provides consumables to incubator |

TABLE 9

Software

| Specification/Function | Comments |
|---|---|
| To comply with automation | Graphical User Interface (GUI) that will give users control over various functions and provide feedback on status and operation of the various processes, sensors, etc. Various levels of automation from manual to automatic modes should be available. |

TABLE 10

Support and Maintenance

| Specification/Function | Comments |
|---|---|
| Service | The system must require no more than 2 preventive maintenance services per annum. |
| Downtime | System malfunction and downtime must be <10% of available operational time. |
| Contamination free | All non-disposable elements must be designed to be easily, rapidly (<2 hours) and thoroughly decontaminated between operations. |
| Contamination free | No detectable sample carry over must be present from one operation to the next. |

We claim:

1. An automated cell culture system comprising: an insertable and removable bioreactor comprising a plurality of cell culture compartments and formed from a plurality of stacked layers including a middle cell culture compartment, the bioreactor having a fluid port fluidly connected to the plurality of cell culture compartments; a pump fluidly connected to the fluid port for providing a cell culture medium to the plurality of culture compartments; a sensor operably connected to at least the middle cell culture compartment for measuring at least one cell culture parameter; one or more actuators operably connected to the middle cell culture compartment configured to automatically control one or more cell culture parameters in the middle cell culture compartment based on an output from the sensor; and a controller electronically connected to the pump, the actuator, and the sensor, wherein the controller is configured to automatically adjust a pump flow rate, a cell culture gas content with a gas exchanger to provide a desired gas composition comprising an appropriate level of each of carbon dioxide, oxygen and nitrogen, and a cell culture parameter to provide an automated desired steady-state cell culture parameter to achieve ideal or desired cell culture conditions based on the output from the sensor for facilitating automated monitoring of cell growth and functional maintenance, cell communication and collection of products from cell interactions; wherein the insertable and removable bioreactor, pump, sensor, gas exchanger and one or more actuators and controller are modularly connected to provide an integrated and automated modular workstation having the insertable and removable bioreactor integrated into the automated modular workstation for tissue co-culture and configured for subsequent removal and shipment to a remote testing facility; wherein a lid and a base plate are positioned to contain the plurality of stacked layers; a fastener to reliably secure the lid top and base plate and fluidly enclose the bioreactor, wherein the plurality of stacked layers are formed of a compressible material; wherein the fastener comprises a clamp that compresses the plurality of stacked layers upon a clamp actuation; and the lid top and base plates have complimentary relief and recess features configured to provide a uniform force distribution over the plurality of stacked layers and provide a fluid seal with the clamp actuation.

2. The cell culture system of claim 1, wherein the plurality of stacked layers comprise
a microbial cell culture compartment layer;
an animal cell culture compartment layer, wherein the animal cell culture compartment layer is optionally for culturing human epithelial cells;
wherein a nanoporous membrane separates the microbial cell culture compartment layer from the animal cell culture compartment layer; and
a perfusion microchamber compartment layer, wherein a microporous membrane separates the perfusion microchamber from the animal cell culture component layer;
wherein the lid and/or base plate have one or more connectors to facilitate access by one or more sensors to the microbial and/or animal cell culture compartment layers.

3. The cell culture system of claim 1, wherein the pump comprises a flow-rate controllable pump, wherein an output from the one or more sensors is used to control a fluid flow rate or pressure from the pump; the cell culture system further comprising a plurality of independently controllable pumps having controlled flow rates of between 1 μL/min to 1 mL/min.

4. The cell culture system of claim 3, wherein an animal cell compartment pump provides animal cell culture medium to the animal cell compartment and a bacterial cell compartment pump provides bacterial cell culture medium to the bacterial cell compartment.

5. The cell culture system of claim 1, wherein the sensor is selected from the group consisting of:
a flow sensor;
a temperature sensor;
a gas sensor;
a pH sensor;
a chemical sensor;
an electrical sensor (electrode);
an optical sensor;
a relative humidity sensor; and
an electromagnetic sensor.

6. The cell culture system of claim 5, comprising a plurality of sensors to measure a plurality of cell culture parameters, wherein the cell culture parameters are selected from the group consisting of one or more of:
flow rate;
temperature;
gas level;
pH level;
chemical level;
electric potential, including a transepithelial electrical resistance (TEER);
optical intensity;
relative humidity;
pressure; and
viscosity.

7. The cell culture system of claim 1, wherein the sensor is positioned to have direct access to a middle channel of the bioreactor.

8. The cell culture system of claim 1, wherein the controller is configured to provide automated and/or remote control of the cell culture system.

9. The cell culture system of claim 1, wherein the one or more actuators in electronic communication with the controller is selected from the group consisting of a heater, an optical light source, a fluid control element, a RF communication component, and a positioning device.

10. The cell culture system of claim 1, wherein the controller is part of a computer, and output from the one or more sensors are displayed and/or electronically stored.

11. The cell culture system of claim 10, comprising at least four separate bioreactors having independently controllable pumps controlled by the controller.

12. The cell culture system of claim 1, further comprising an incubator having an incubation volume, wherein the bioreactor has a size and geometric shape to fit within the incubation volume.

13. The cell culture system of claim 1, further comprising a first electrode inlaid in the lid and a second electrode in the base plate for continuous monitoring of an electrical resistance in the bioreactor.

14. The cell culture system of claim 1, the gas exchanger further comprising:
a holder configured to hold a gas permeable tube in a reeled-up geometry, wherein the gas permeable tube is connected to the bioreactor fluid port; and
a gas chamber having an enclosure, wherein the holder is positioned in the enclosure to thereby provide a controlled gas exchange between the gas chamber and a lumen of the gas permeable tube.

15. A method of co-culturing a plurality of distinct cell types, the method comprising the steps of:
providing the cell culture system of claim 1;
establishing a first cell culture in a first cell culture compartment;
establishing a second cell culture in a second cell culture compartment, wherein the first cell culture and the second cell culture comprise different cell types;
activating the pump to force fluid medium through the fluid compartments at a first fluid flow rate in the first fluid compartment and a second fluid flow rate in the second fluid compartment;
monitoring a cell culture parameter in each of the first cell culture compartment and the second cell culture compartment with one or more sensors in each of the cell culture compartments;
adjusting the first and/or the second fluid flow rates and/or cell culture gas inflow to maintain the cell culture parameter in each of the first cell culture compartment and the second cell culture compartment;
thereby co-culturing the plurality of distinct cell types.

16. The method of claim 15, wherein the first cell type comprises an animal cell and the second cell type comprises bacteria.

17. The method of claim 15, wherein the activating, monitoring and adjusting steps are automatically controlled by a controller receiving output signals from the sensors, wherein the co-culturing occurs for a time period of at least three days without active intervention.

18. The method of claim 15, wherein the cell culture gas inflow comprises passing culture gas through the gas exchanger.

19. The cell culture of claim 1, further comprising a top inlaid electrode on a top surface of the middle cell culture compartment and a bottom inlaid electrode on a bottom surface of the middle cell culture compartment for continuous monitoring of transepithelial electrical resistance (TEER) and characterization of oxygen permeation and hypoxia.

20. The cell culture of claim 1, wherein the lid and the base plate are formed from a plastic such as polycarbonate.

* * * * *